(12) United States Patent
Singh et al.

(10) Patent No.: US 9,156,908 B2
(45) Date of Patent: Oct. 13, 2015

(54) HIGH AFFINITY, ANTI-HUMAN IGE ANTIBODIES

(71) Applicant: TANOX, INC., Houston, TX (US)

(72) Inventors: Sanjaya Singh, Sandy Hook, CT (US); Herren Wu, Boyds, MD (US); Catherine Foster, Dumont, NJ (US)

(73) Assignee: TANOX, INC., Houston, TX (US)

( * ) Notice: Subject to any disclaimer, the term of this patent is extended or adjusted under 35 U.S.C. 154(b) by 148 days.

(21) Appl. No.: 14/074,309

(22) Filed: Nov. 7, 2013

(65) Prior Publication Data

US 2014/0295494 A1 Oct. 2, 2014

Related U.S. Application Data

(60) Division of application No. 13/559,938, filed on Jul. 27, 2012, now Pat. No. 8,604,171, which is a continuation of application No. 12/413,014, filed on Mar. 27, 2009, now Pat. No. 8,252,284, which is a continuation of application No. 10/544,056, filed as application No. PCT/US2004/002894 on Feb. 2, 2004, now Pat. No. 7,531,169.

(60) Provisional application No. 60/444,229, filed on Feb. 1, 2003.

(51) Int. Cl.

| C07K 16/18 | (2006.01) |
| C12N 15/63 | (2006.01) |
| C07H 21/04 | (2006.01) |
| C12P 21/08 | (2006.01) |
| C12N 15/09 | (2006.01) |
| C07K 16/00 | (2006.01) |
| C07K 16/42 | (2006.01) |
| G01N 33/68 | (2006.01) |

(52) U.S. Cl.
CPC ............... C07K 16/18 (2013.01); C07K 16/005 (2013.01); C07K 16/4291 (2013.01); G01N 33/6854 (2013.01); C07K 2317/24 (2013.01); C07K 2317/55 (2013.01); C07K 2317/565 (2013.01); C07K 2317/567 (2013.01); G01N 2800/24 (2013.01); Y10S 435/81 (2013.01)

(58) Field of Classification Search
CPC .. C07K 16/005; C07K 16/4291; C07K 16/18; C07K 2317/24; C07K 2317/56; C07K 2317/567; C12N 5/10; C12N 5/16; C12N 7/02; C12N 15/70; C12N 2800/10; C12N 2330/5061

See application file for complete search history.

(56) References Cited

U.S. PATENT DOCUMENTS

| 5,091,313 A | 2/1992 | Chang | |
| 5,428,133 A | 6/1995 | Chang | |
| 5,543,144 A | 8/1996 | Chang | |
| 5,614,611 A | 3/1997 | Chang | |
| 7,531,169 B2 * | 5/2009 | Singh et al. | 424/130.1 |
| 8,252,284 B2 * | 8/2012 | Singh et al. | 424/130.1 |
| 8,604,171 B2 * | 12/2013 | Singh et al. | 530/387.1 |
| 2005/0169909 A1 | 8/2005 | Singh et al. | |
| 2006/0234296 A1 | 10/2006 | Singh et al. | |

FOREIGN PATENT DOCUMENTS

| EP | 0 407 392 | 1/1991 |
| WO | WO 92/17207 | 10/1992 |
| WO | WO 99/62550 | 12/1999 |

OTHER PUBLICATIONS

Babu et al., 2001, "Anti-IgE treatment: an update" Allergy 56:1121-1128.
Boulet et al., 1997, "Inhibitory effects of an anti-IgE antibody E25 on allergen-induced early asthmatic response." Am J. Resp. Crit. Care. Med. 155:1835-1840.
Chang et al., 1990, "Monoclonal Antibodies Specific for Human IgE-Producing B Cells: A Potential Therapeutic for IgE-Mediated Allergic Diseases" Biotech 8(2):122-126.
Corne et al., 1997. "The effect of intravenous administration of a chimeric anti-IgE antibody on serum IgE levels in atopic subjects: efficacy, safety, and pharmacokinetics." J. Clin Invest 99:879-887.
Fahy et al., 1997, The effect of an anti-IgE monoclonal antibody on the early- and late-phase responses to allergen inhalation in asthmatic subjects Am. J. resp. Crit. Care Med 155:1828-1834.
Klubal et al, , 1997, "The high-affinity receptor for IgE is the predominant IgE-binding structure in lesional skin of atopic dermatitis patients." J Invest. Dermatol 108(3):336-42.
MacGlashan et al., 1997, "Down-regulation of Fc(epsilon)RI expression on human basophils during in vivo treatment of atopic patients with anti-IgE antibody." J. Immunol. 158:1438-1445.
Malveaux, 1978, "IgE receptors on human basophils. Relationship to serum IgE concentration." J Clin. Invest 62:176.
Milgrom et al., 1999, "Treatment of allergic asthma with monoclonal anti-IgE antibody. rhuMAb-E25 Study Group." N. Engl, J Med 341:1966-1973.
Racine-Poon, et al., 1997, "Efficacy, pharmacodynamics, and pharmacokinetics of CGP 51901, an anti-immunoglobulin E chimeric monoclonal antibody, in patients with seasonal allergic rhinitis." Clin. Pharmacol. Ther. 62:675-690.
Schulman, 2001, "Development of Monocloncal Anti-Immunoglobulin E Antibody (Omalizub) for the treatment of allergic respiratory disorders." Am J. Resp. Crit. Care Med. 164 :S6-S11.

* cited by examiner

*Primary Examiner* — Phuong Huynh
(74) *Attorney, Agent, or Firm* — Jones Day

(57) ABSTRACT

The invention relates to high affinity human monoclonal antibodies, particularly those directed against isotypic determinants of immunoglobulin E (IgE), as well as direct equivalents and derivatives of these antibodies. These antibodies bind to their respective target with an affinity at least 100 fold greater than the original parent antibody. These antibodies are useful for diagnostics, prophylaxis and treatment of disease.

21 Claims, 17 Drawing Sheets

Figure 1 Phage Vector

Figure 3   TES-C21 and Template Comparison

A.   Light Chain (V<sub>K</sub>) (Underlined: Kabat CDR. Bold/Italic: Chothia CDR) (TES-C21 LIGHT CHAIN – SEQ ID NO 1   L16/JK4 – SEQ ID NO 2)

```
                        10                  20                  30
Mu TES-C21    D I L L T Q S P A I L S V S P G E R V S F S C R A S Q S I G T N I H W Y Q Q
L16 VK        E V M           T                           A T L   R A S Q S V S S N L A 40                  50                  60                  70
TES-C21       K T D G S P R L L I K Y A S E S I S G I P S R F S G S G S G T E F T L N I N
L16 VK        K P G Q A                   Y G A S T R A T                           T S 80                  90                 100       107
TES-C21       S V E S E D I A D Y Y C Q Q S D S W P T T F G G G T K L E I K
L16 VK-JK4    L Q     P   V       Q Q Y N N W P L T                 V
```

B.   Heavy Chain (V<sub>H</sub>)
TES-C21 HEAVY CHAIN – SEQ ID NO 3    DP88/JH4b – SEQ ID NO 4

```
                     1                 10                  20                  30
Murine TES-C21   Q V Q L Q Q S G A E L M K P G A S V K I S C K T T G Y T F S M Y W L E W V
DP88 VH                      V                                 V 40                  50  52a 53               60                  65  70
TES-C21          K Q R P G H G L E W V G E I S P G T F T T N Y N E K F K A K A T F T A D T
DP88 VH            R   A   Q             M   G I I P I F G T A N Y A Q K F Q G R V   I   K 80  82a b c 83            90                  95             100 b c d e f 101
TES-C21          S S N T A Y L Q L S G L T S E D S A V Y F C A R P S H F S G S N Y D Y F D Y
DP88 VH          T S       M E   S     R       T   Y                 - - - - - - Y F D Y 103           110 113
TES-C21          W G Q G T S L T V S S
DP88-JH4b          L V
```

Figure 4  Framework Sequences of High Affinity Candidates*

| VK Positions | 1 | 3 | 4 | 49 | 60 | 85 | VH Positions | 12 | 27 | 43 | 48 | 67 | 69 |
|---|---|---|---|---|---|---|---|---|---|---|---|---|---|
| Mouse | D | L | L | K | S | D | Mouse | M | Y | H | V | A | F |
| Human | E | V | M | Y | A | V | Human | K | G | Q | M | V | I |
| 1 (clone ID) | D | L | M | K | S | V |  | M | Y | H | M | A | F |
| 2 | D | V | L | K | A | V |  | K | Y | Q | M | V | F |
| 4 | D | L | L | Y | S | V |  | M | Y | Q | M | V | F |
| 8 | D | V | M | Y | S | V |  | M | Y | Q | V | A | F |
| 13 | E | V | L | K | A | D |  | K | Y | Q | M | A | F |
| 15 | D | L | M | Y | A | V |  | M | Y | Q | V | V | F |
| 16 | D | L | M | Y | A | V |  | M | Y | Q | M | V | F |
| 18 | E | L | L | K | S | D |  | M | Y | Q | M | V | F |
| 21 | D | V | L | Y | A | V |  | M | Y | H | V | V | F |
| 23 | E | L | L | K | A | D |  | M | Y | Q | M | V | F |
| 25 | D | V | M | Y | A | V |  | M | Y | Q | V | A | F |
| 27 | E | L | M | Y | S | D |  | M | Y | Q | V | V | F |
| 30 | E | V | L | Y | A | D |  | K | Y | Q | V | V | F |
| 31 | E | V | L | Y | A | V |  | M | Y | H | V | A | F |
| 33 | E | V | L | Y | S | V |  | K | Y | Q | M | V | F |
| 35 | E | V | M | Y | A | D |  | K | Y | H | M | V | F |
| 38 | E | V | M | K | A | D |  | K | Y | Q | M | V | F |
| 43 | E | V | L | Y | S | V |  | M | Y | H | M | V | I |
| 44 | E | V | L | Y | A | D |  | M | Y | H | V | V | I |
| 45 | E | V | M | K | A | V |  | M | Y | Q | M | V | F |
| 46 | E | V | L | K | S | V |  | M | Y | H | V | V | F |
| 48 | E | V | M | Y | A | D |  | M | Y | H | V | V | F |
| 49 | E | V | M | Y | A | V |  | M | Y | Q | M | V | F |
| 50 | D | L | L | Y | A | D |  | M | Y | H | V | A | F |
| 52 | E | L | L | Y | A | D |  | K | Y | Q | V | V | F |
| 53 | D | V | L | Y | S | V |  | M | Y | H | V | M | V |
| 56 | D | L | M | Y | S | V |  | M | Y | H | M | A | F |
| 58 | D | V | M | K | S | V |  | M | Y | H | M | V | F |
| 61 | D | V | M | K | S | V |  | M | Y | H | M | V | F |
| 63 | D | V | L | K | S | V |  | K | Y | Q | V | V | F |
| 64 | E | V | M | K | S | D |  | M | Y | Q | V | V | F |
| 66 | D | V | L | Y | S | V |  | M | Y | Q | V | V | F |
| 70 | D | V | L | Y | A | D |  | K | Y | Q | M | A | F |
| 72 | D | V | L | Y | A | V |  | M | Y | H | M | V | F |
| 75 | E | L | L | K | S | V |  | K | Y | Q | M | A | F |
| 76 | D | V | M | Y | S | V |  | M | Y | Q | M | A | F |
| 78 | D | V | M | Y | S | V |  | M | Y | Q | M | V | F |
| 81 | E | V | L | K | S | D |  | M | Y | Q | M | A | F |
| 83 | E | V | L | K | A | D |  | M | Y | H | V | V | F |
| 86 | E | L | M | K | A | V |  | M | Y | Q | M | V | F |
| 89 | E | L | M | Y | A | V |  | M | Y | H | V | V | F |
| 90 | D | V | M | Y | A | D |  | K | Y | H | V | V | F |
| 93 | E | L | M | K | A | V |  | M | Y | Q | V | A | F |
| 103 | D | V | L | Y | A | V |  | M | Y | Q | V | A | I |
| 109 | D | L | L | K | S | V |  | M | Y | H | M | A | F |
| 114 | D | L | L | Y | A | V |  | M | Y | Q | V | V | F |
| 124 | E | V | L | Y | S | D |  | K | Y | Q | V | V | F |
| 128 | D | V | M | Y | A | V |  | M | Y | Q | V | V | F |
| 135 | D | V | L | K | S | V |  | M | Y | Q | M | V | F |
| 136 | E | V | M | Y | A | V |  | M | Y | H | M | V | F |
| 152 | E | V | L | Y | S | V |  | M | Y | H | V | V | F |
| 153 | D | L | L | Y | S | V |  | K | Y | Q | M | V | F |
| 157 | D | L | M | Y | S | D |  | K | Y | Q | M | V | F |
| 1136-2C | E | V | M | Y | S | D |  | K | Y | Q | M | V | F |

*P=parent sequence; T=human template sequence; amino acids listed in bold are murine residues Figure 5  ELISA TITRATION CURVE
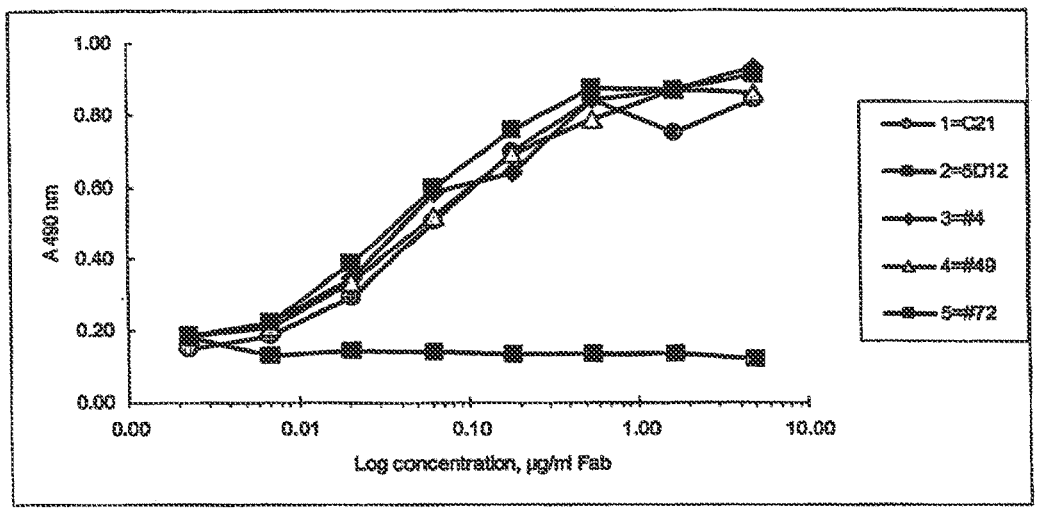
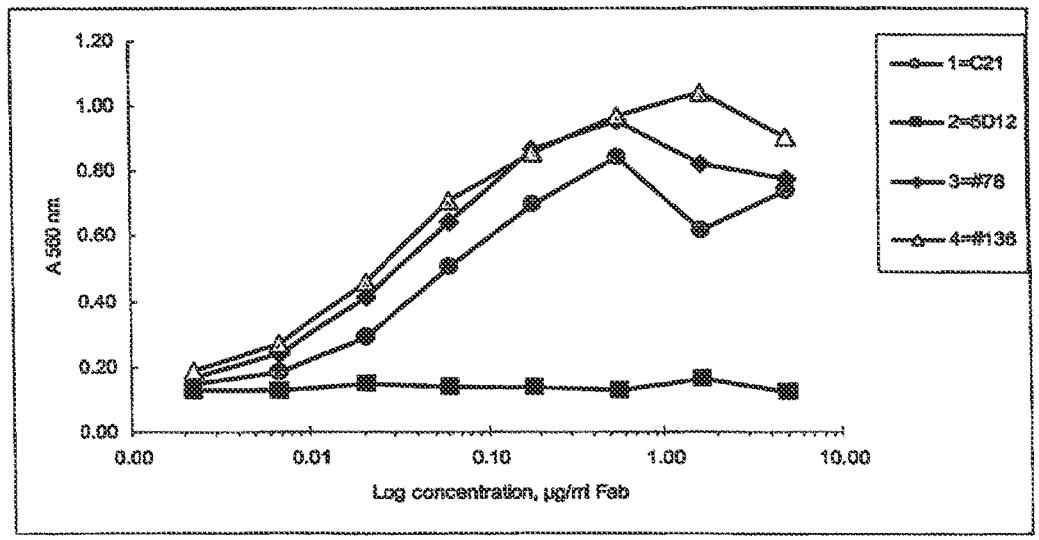

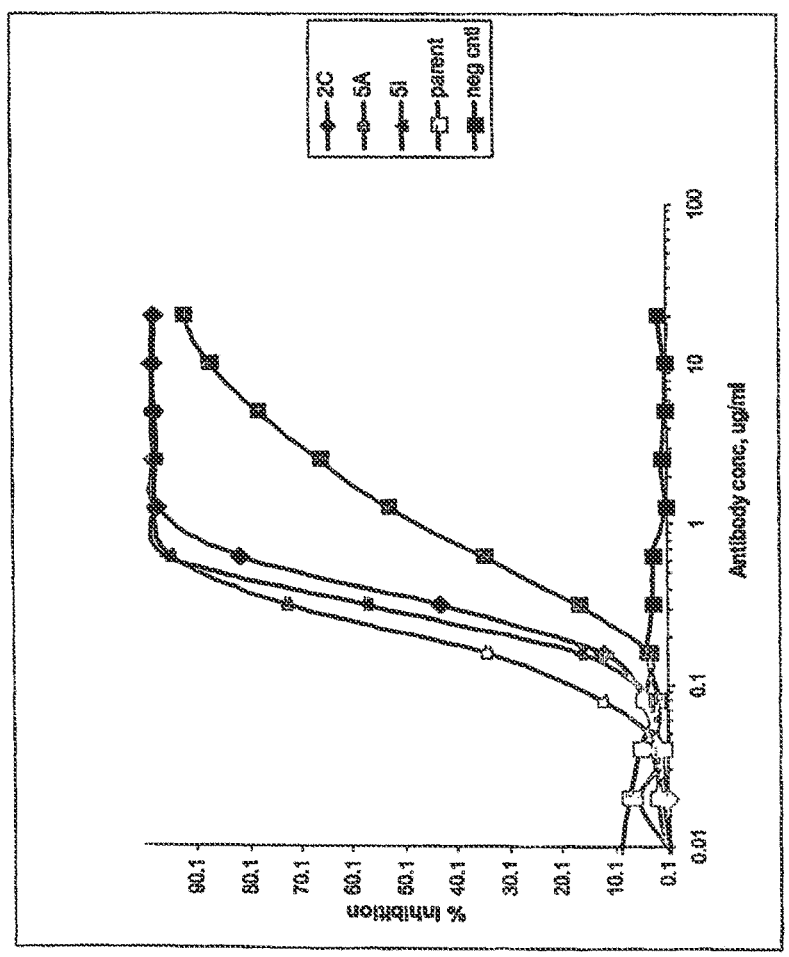
Figure 6 Inhibition Assay

Figure 7: List of High Affinity Candidates from Library

| Clone | CDR-L1 | CDR-L2 | CDR-L3 | CDR-H1 | CDR-H2 | CDR-H3 |
|---|---|---|---|---|---|---|
| 136 | RASRSIGTNIH | YASESIS | QQSASWPTT | MYWLE | EISPGTFTTNYNEKFKA | FSHFSGSNYDYFDY |
| L3-9 | wt | wt | QQSWSWPTT | wt | wt | wt |
| CL-2G | wt | wt | QQSWSWPTT | WYWLE | wt | wt |
| R5-E | wt | wt | QQSWSWPTT | YYWLE | wt | wt |
| R87-E | wt | wt | QQSWSWPTT | wt | EIEPGTFTTNYNEKFKA | wt |
| CL-2I | wt | wt | QQSWSWPTT | wt | EIDPGTFTTNYNEKFKA | wt |
| R2-C | wt | wt | QQSWSWPTT | WYWLE | EIEPGTFTTNYNEKFKA | wt |
| CL-2C | wt | wt | QQSWSWPTT | WYWLE | EIEPGTFTTNYNEKFKA | wt |
| CL-2H | wt | wt | QQSWSWPTT | YYWLE | EIEPGTFTTNYNEKFKA | wt |
| CL-2B | wt | wt | QQSWSWPTT | YYWLE | EIDPGTFTTNYNEKFKA | wt |
| CL-3A | wt | wt | QQSWSWPTT | wt | EISPETFTTNYNEKFKA | wt |
| R47-E | wt | wt | QQSWSWPTT | wt | EISPDTFTTNYNEKFKA | wt |
| CL-3G | wt | wt | QQSWSWPTT | YYWLE | EISPETFTTNYNEKFKA | wt |
| R3-A | wt | wt | QQSWSWPTT | YYWLE | EISPDTFTTNYNEKFKA | wt |
| CL-3C | wt | wt | QQSWSWPTT | WYWLE | EISPETFTTNYNEKFKA | wt |
| CL-3E | wt | wt | QQSWSWPTT | WYWLE | EISPDTFTTNYNEKFKA | wt |
| R5-K | wt | wt | QQSWSWPTT | wt | EISPGTFETNYNEKFKA | wt |
| CL-4B | wt | wt | QQSWSWPTT | WYWLE | EISPGTFETNYNEKFKA | wt |
| R5-D | wt | wt | QQSWSWPTT | YYWLE | EIEPGTFETNYNEKFKA | wt |
| CL-5G | wt | wt | QQSWSWPTT | wt | EIEPGTFETNYNEKFKA | wt |
| CL-5I | wt | wt | QQSWSWPTT | wt | EIDPGTFETNYNEKFKA | wt |
| CL-5A | wt | wt | QQSWSWPTT | WYWLE | EIEPGTFETNYNEKFKA | wt |
| CL-5H | wt | wt | QQSWSWPTT | WYWLE | EIDPGTFETNYNEKFKA | wt |
| R5-H | wt | wt | QQSWSWPTT | YYWLE | EIEPGTFETNYNEKFKA | wt |
| R5-N | wt | wt | QQSWSWPTT | YYWLE | EIDPGTFETNYNEKFKA | wt |

Changes from parent amino acid sequence are listed in BOLD.

FIGURE 8A

VK Alignment

| | 1 | 2 | 3 | 4 | 5 | 6 | 7 | 8 | 9 | # | # | # | # | # | # | # | # | 20 | 21 | 22 | 23 | SEQ ID | 24-34 CDR-L1 | 35 | 36 | 37 | 38 | 39 | 40 | 41 | 42 | 43 | 44 | 45 | 46 | 47 | 48 | 49 | SEQ ID | 50-56 CDR-L2 |
|---|---|---|---|---|---|---|---|---|---|---|---|---|---|---|---|---|---|---|---|---|---|---|---|---|---|---|---|---|---|---|---|---|---|---|---|---|---|---|---|---|
| 136 | E | I | V | M | T | Q | S | P | A | T | L | S | V | S | P | G | E | R | A | T | L | S | C | 38 | | W | Y | Q | Q | K | P | G | Q | A | P | R | L | L | – | Y | 39 | |
| 1 | D | I | – | L | – | T | Q | S | P | A | T | L | S | V | S | P | G | E | R | A | T | L | S | C | 30 | | W | Y | Q | Q | K | P | G | Q | A | P | R | L | L | – | Y | | |
| 2 | D | I | V | L | – | T | Q | S | P | A | T | L | S | V | S | P | G | E | R | A | T | L | S | C | 31 | | W | Y | Q | Q | K | P | G | Q | A | P | R | L | L | – | K | | |
| 4 | D | I | – | L | – | T | Q | S | P | A | T | L | S | V | S | P | G | E | R | A | T | L | S | C | 32 | | W | Y | Q | Q | K | P | G | Q | A | P | R | L | L | – | K | | |
| 13 | E | I | V | L | – | T | Q | S | P | A | T | L | S | V | S | P | G | E | R | A | T | L | S | C | 33 | | W | Y | Q | Q | K | P | G | Q | A | P | R | L | L | – | Y | | |
| 15 | D | I | – | M | – | T | Q | S | P | A | T | L | S | V | S | P | G | E | R | A | T | L | S | C | 34 | | W | Y | Q | Q | K | P | G | Q | A | P | R | L | L | – | K | | |
| 18 | E | I | V | L | – | T | Q | S | P | A | T | L | S | V | S | P | G | E | R | A | T | L | S | C | | | W | Y | Q | Q | K | P | G | Q | A | P | R | L | L | – | K | | |
| 23 | D | I | – | L | – | T | Q | S | P | A | T | L | S | V | S | P | G | E | R | A | T | L | S | C | 35 | | W | Y | Q | Q | K | P | G | Q | A | P | R | L | L | – | Y | | |
| 25 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 27 | D | I | – | M | – | T | Q | S | P | A | T | L | S | V | S | P | G | E | R | A | T | L | S | C | 36 | | W | Y | Q | Q | K | P | G | Q | A | P | R | L | L | – | Y | | |
| 30 | D | I | V | L | – | T | Q | S | P | A | T | L | S | V | S | P | G | E | R | A | T | L | S | C | 37 | | W | Y | Q | Q | K | P | G | Q | A | P | R | L | L | – | Y | | |
| 31 | E | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 33 | D | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 35 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 38 | D | I | V | M | – | T | Q | S | P | A | T | L | S | V | S | P | G | E | R | A | T | L | S | C | | | W | Y | Q | Q | K | P | G | Q | A | P | R | L | L | – | K | | |
| 45 | E | I | V | L | – | T | Q | S | P | A | T | L | S | V | S | P | G | E | R | A | T | L | S | C | | | W | Y | Q | Q | K | P | G | Q | A | P | R | L | L | – | K | | |
| 46 | D | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 50 | D | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 52 | D | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 53 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 56 | D | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 58 | D | I | V | L | – | T | Q | S | P | A | T | L | S | V | S | P | G | E | R | A | T | L | S | C | | | W | Y | Q | Q | K | P | G | Q | A | P | R | L | L | – | K | | |
| 63 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 64 | D | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 70 | D | I | V | L | – | T | Q | S | P | A | T | L | S | V | S | P | G | E | R | A | T | L | S | C | | | W | Y | Q | Q | K | P | G | Q | A | P | R | L | L | – | K | | |
| 72 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 75 | E | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 78 | D | I | V | L | – | T | Q | S | P | A | T | L | S | V | S | P | G | E | R | A | T | L | S | C | | | W | Y | Q | Q | K | P | G | Q | A | P | R | L | L | – | K | | |
| 81 | E | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 86 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 89 | E | I | V | M | – | T | Q | S | P | A | T | L | S | V | S | P | G | E | R | A | T | L | S | C | | | W | Y | Q | Q | K | P | G | Q | A | P | R | L | L | – | K | | |
| 90 | E | I | V | M | – | T | Q | S | P | A | T | L | S | V | S | P | G | E | R | A | T | L | S | C | | | W | Y | Q | Q | K | P | G | Q | A | P | R | L | L | – | Y | | |
| 109 | D | I | V | L | – | T | Q | S | P | A | T | L | S | V | S | P | G | E | R | A | T | L | S | C | | | W | Y | Q | Q | K | P | G | Q | A | P | R | L | L | – | Y | | |
| 114 | D | I | – | L | – | T | Q | S | P | A | T | L | S | V | S | P | G | E | R | A | T | L | S | C | | | W | Y | Q | Q | K | P | G | Q | A | P | R | L | L | – | K | | |
| 124 | E | I | V | L | – | T | Q | S | P | A | T | L | S | V | S | P | G | E | R | A | T | L | S | C | | | W | Y | Q | Q | K | P | G | Q | A | P | R | L | L | – | Y | | |

VH alignments

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | SEQ ID | 31-35 CDR-H1 | 36 | 37 | 38 | 39 | 40 | 41 | 42 | 43 | 44 | 45 | 46 | 47 | 48 | 49 | SEQ ID | 50-66 CDR-H2 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 136 | Q | V | Q | L | V | Q | S | G | A | E | V | M | K | P | G | S | S | V | K | V | S | C | K | A | S | G | Y | T | F | S | 45 | | W | V | R | Q | A | P | G | H | G | L | E | W | M | G | 47 | |
| 1 | Q | V | Q | L | V | Q | S | G | A | E | V | M | K | P | G | S | S | V | K | V | S | C | K | A | S | G | Y | T | F | S | 46 | | W | V | R | Q | A | P | G | Q | G | L | E | W | M | G | | |
| 2 | Q | V | Q | L | V | Q | S | G | A | E | V | M | K | P | G | S | S | V | K | V | S | C | K | A | S | G | Y | T | F | S | | | W | V | R | Q | A | P | G | Q | G | L | E | W | M | G | 48 | |
| 4 | Q | V | Q | L | V | Q | S | G | A | E | V | V | K | P | G | S | S | V | K | V | S | C | K | A | S | G | Y | T | F | S | | | W | V | R | Q | A | P | G | Q | G | L | E | W | M | G | 49 | |
| 8 | Q | V | Q | L | V | Q | S | G | A | E | V | M | K | P | G | S | S | V | K | V | S | C | K | A | S | G | Y | T | F | S | | | W | V | R | Q | A | P | G | Q | G | L | E | W | V | G | | |
| 13 | Q | V | Q | L | V | Q | S | G | A | E | V | M | K | P | G | S | S | V | K | V | S | C | K | A | S | G | Y | T | F | S | | | W | V | R | Q | A | P | G | Q | G | L | E | W | M | G | 50 | |
| 15 | Q | V | Q | L | V | Q | S | G | A | E | V | V | K | P | G | S | S | V | K | V | S | C | K | A | S | G | Y | T | F | S | | | W | V | R | Q | A | P | G | Q | G | L | E | W | V | G | | |
| 21 | Q | V | Q | L | V | Q | S | G | A | E | V | M | K | P | G | S | S | V | K | V | S | C | K | A | S | G | Y | T | F | S | | | W | V | R | Q | A | P | G | Q | G | L | E | W | M | G | | |
| 30 | Q | V | Q | L | V | Q | S | G | A | E | V | K | K | P | G | S | S | V | K | V | S | C | K | A | S | G | Y | T | F | S | | | W | V | R | Q | A | P | G | Q | G | L | E | W | V | G | | |
| 31 | Q | V | Q | L | V | Q | S | G | A | E | V | V | K | P | G | S | S | V | K | V | S | C | K | A | S | G | Y | T | F | S | | | W | V | R | Q | A | P | G | Q | G | L | E | W | V | G | | |
| 35 | Q | V | Q | L | V | Q | S | G | A | E | V | K | K | P | G | S | S | V | K | V | S | C | K | A | S | G | Y | T | F | S | | | W | V | R | Q | A | P | G | H | G | L | E | W | M | G | | |
| 43 | Q | V | Q | L | V | Q | S | G | A | E | V | M | K | P | G | S | S | V | K | V | S | C | K | A | S | G | Y | T | F | S | | | W | V | R | Q | A | P | G | H | G | L | E | W | V | G | | |
| 44 | Q | V | Q | L | V | Q | S | G | A | E | V | V | K | P | G | S | S | V | K | V | S | C | K | A | S | G | Y | T | F | S | | | W | V | R | Q | A | P | G | H | G | L | E | W | M | G | | |
| 53 | Q | V | Q | L | V | Q | S | G | A | E | V | V | K | P | G | S | S | V | K | V | S | C | K | A | S | G | Y | T | F | S | | | W | V | R | Q | A | P | G | H | G | L | E | W | M | G | | |
| 81 | Q | V | Q | L | V | Q | S | G | A | E | V | K | K | P | G | S | S | V | K | V | S | C | K | A | S | G | Y | T | F | S | | | W | V | R | Q | A | P | G | H | G | L | E | W | V | G | | |
| 90 | Q | V | Q | L | V | Q | S | G | A | E | V | M | K | P | G | S | S | V | K | V | S | C | K | A | S | G | Y | T | F | S | | | W | V | R | Q | A | P | G | H | G | L | E | W | M | G | | |
| 103 | Q | V | Q | L | V | Q | S | G | A | E | V | V | K | P | G | S | S | V | K | V | S | C | K | A | S | G | Y | T | F | S | | | W | V | R | Q | A | P | G | Q | G | L | E | W | V | G | | |

FIGURE 9B

| 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | SEQ ID | 99-112 | 113 | 114 | 115 | 116 | 117 | 118 | 119 | 120 | 121 | 122 | 123 | 55 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| R | V | T | F | T | A | D | T | S | T | S | T | A | Y | M | E | L | S | S | L | R | S | E | D | T | A | V | Y | Y | C | A | R | 51 | CDR-H3 |   |   |   |   |   |   |   |   |   |   |   |   |
| R | A | T | F | T | A | D | T | S | T | S | T | A | Y | M | E | L | S | S | L | R | S | E | D | T | A | V | Y | Y | C | A | R | 52 |   | W | G | Q | G | T | L | V | T | V | S | S |   |
| R | V | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | V | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | V | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | V | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | F | T | A | D | T | S | T | S | T | A | Y | M | E | L | S | S | L | R | S | E | D | T | A | V | Y | Y | C | A | R | 53 |   | W | G | Q | G | T | L | V | T | V | S | S |   |
| R | V | T | — | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | V | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | F | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | V | T | — | T | A | D | T | S | T | S | T | A | Y | M | E | L | S | S | L | R | S | E | D | T | A | V | Y | Y | C | A | R |   |   | W | G | Q | G | T | L | V | T | V | S | S |   |
| R | A | T | — | T | A | D | T | S | T | S | T | A | Y | M | E | L | S | S | L | R | S | E | D | T | A | V | Y | Y | C | A | R | 54 |   | W | G | Q | G | T | L | V | T | V | S | S |   |

Figure 10A Polypeptide sequence of Mab 136

LIGHT CHAIN

SIGNAL PEPTIDE

MEWSGVFMFLLSVTAGVHS    (SEQ ID NO 56)

VARIABLE REGION Vk

EIVMTQSPAT LSVSPGERAT LSCRASQSIG TNIHWYQQKP GQAPRLLIYY
ASESISGIPA RFSGSGSGTE FTLTISSLQS EDFAVYYCQQ SDSWPTTFGG
GTKVEIK                (SEQ ID NO 57)

CONSTANT REGION Ck

TVAAPSVFIF PPSDEQLKSG TASVVCLLNN FYPREAKVQW KVDNALQSGN
SQESVTEQDS KDSTYSLSST LTLSKADYEK HKVYACEVTH QGLSSPVTKS
FNRGEC                 (SEQ ID NO 58)

HEAVY CHAIN (IgG1)

SIGNAL PEPTIDE

MEWSGVFMFLLSVTAGVHS    (SEQ ID NO 56)

VARIABLE REGION VH

QVQLVQSGAE VMKPGSSVKV SCKASGYTFS MYWLEWVRQA PGHGLEWMGE
ISPGTFTTNY NEKFKARVTF TADTSTSTAY MELSSLRSED TAVYYCARFS
HFSGSNYDYF DYWGQGTLVT VSS            (SEQ ID NO 59)

CONSTANT REGION CH1-3(IgG1)        (SEQ ID NO 60)

ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

Figure 10B Polypeptide Sequence of MAb CL-2C

LIGHT CHAIN

SIGNAL PEPTIDE

MEWSGVFMFLLSVTAGVHS          (SEQ ID NO 56)

VARIABLE REGION Vk

EIVMTQSPAT LSVSPGERAT LSCRASQSIG TNIHWYQQKP GQAPRLLIYY
ASESISGIPA RFSGSGSGTE FTLTISSLQS EDFAVYYCQQ SWSWPTTFGG
GTKVEIK            (SEQ ID NO 61)

CONSTANT REGION Ck

TVAAPSVFIF PPSDEQLKSG TASVVCLLNN FYPREAKVQW KVDNALQSGN
SQESVTEQDS KDSTYSLSST LTLSKADYEK HKVYACEVTH QGLSSPVTKS
FNRGEC              (SEQ ID NO 58)

HEAVY CHAIN (IgG1)

SIGNAL PEPTIDE

MEWSGVFMFLLSVTAGVHS          (SEQ ID NO 56)

VARIABLE REGION VH (2C)

QVQLVQSGAE VMKPGSSVKV SCKASGYTFS WYWLEWVRQA PGHGLEWMGE
IDPGTFTTNY NEKFKARVTF TADTSTSTAY MELSSLRSED TAVYYCARFS
HFSGSNYDYF DYWGQGTLVT VSS       (SEQ ID NO 62)

CONSTANT REGION CH1-3(IgG1)      (SEQ ID NO 60)

ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

Figure 10C Polypeptide Sequence of MAb CL-SI

LIGHT CHAIN

SIGNAL PEPTIDE

MEWSGVFMFLLSVTAGVHS    (SEQ ID NO 56)

VARIABLE REGION Vk

EIVMTQSPAT LSVSPGERAT LSCRASQSIG TNIHWYQQKP GQAPRLLIYY
ASESISGIPA RFSGSGSGTE FTLTISSLQS EDFAVYYCQQ SWSWPTTFGG
GTKVEIK    (SEQ ID NO 63)

CONSTANT REGION Ck    (SEQ ID NO 58)

TVAAPSVFIF PPSDEQLKSG TASVVCLLNN FYPREAKVQW KVDNALQSGN
SQESVTEQDS KDSTYSLSST LTLSKADYEK HKVYACEVTH QGLSSPVTKS
FNRGEC

HEAVY CHAIN (IgG1)

SIGNAL PEPTIDE

MEWSGVFMFLLSVTAGVHS    (SEQ ID NO 56)

VARIABLE REGION VH (SI)

QVQLVQSGAE VMKPGSSVKV SCKASGYTFS MYWLEWVRQA PGHGLEWMGE
IDPGTFETNY NEKFKARVTF TADTSTSTAY MELSSLRSED TAVYYCARFS
HFSGSNYDYF DYWGQGTLVT VSS    (SEQ ID NO 64)

CONSTANT REGION CH1-3(IgG1)    (SEQ ID NO 60)

ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

Figure 10D  Polypeptide Sequence of MAb CL-5A

LIGHT CHAIN

SIGNAL PEPTIDE

MEWSGVFMFLLSVTAGVHS    (SEQ ID NO 56)

VARIABLE REGION Vk

EIVMTQSPAT LSVSPGERAT LSCRASQSIG TNIHWYQQKP GQAPRLLIYY
ASESISGIPA RFSGSGSGTE FTLTISSLQS EDFAVYYCQQ SWSWPTTFGG
GTKVEIK    (SEQ ID NO 65)

CONSTANT REGION Ck    (SEQ ID NO 58)

TVAAPSVFIF PPSDEQLKSG TASVVCLLNN FYPREAKVQW KVDNALQSGN
SQESVTEQDS KDSTYSLSST LTLSKADYEK HKVYACEVTH QGLSSPVTKS
FNRGEC

HEAVY CHAIN (IgG1)

SIGNAL PEPTIDE

MEWSGVFMFLLSVTAGVHS    (SEQ ID NO 56)

VARIABLE REGION VH (5A)

QVQLVQSGAE VMKPGSSVKV SCKASGYTFS WYWLEWVRQA PGHGLEWMGE
IEPGTETTNY NEKFKARVTF TADTSTSTAY MELSSLRSED TAVYYCARFS
HFSGSNYDYF DYWGQGTLVT VSS    (SEQ ID NO 66)

CONSTANT REGION CH1-3(IgG1)    (SEQ ID NO 60)

ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

Figure 10E Polypeptide Sequence of MAb CL-2B

LIGHT CHAIN

SIGNAL PEPTIDE

MEWSGVFMFLLSVTAGVHS          (SEQ ID NO 56)

VARIABLE REGION Vk

EIVMTQSPAT LSVSPGERAT LSCRASQSIG TNIHWYQQKP GQAPRLLIYY
ASESISGIPA RFSGSGSGTE FTLTISSLQS EDFAVYYCQQ SWSWPTTFGG
GTKVEIK          (SEQ ID NO 67)

CONSTANT REGION Ck     (SEQ ID NO 58)

TVAAPSVFIF PPSDEQLKSG TASVVCLLNN FYPREAKVQW KVDNALQSGN
SQESVTEQDS KDSTYSLSST LTLSKADYEK HKVYACEVTH QGLSSPVTKS
FNRGEC

HEAVY CHAIN (IgG1)

SIGNAL PEPTIDE

MEWSGVFMFLLSVTAGVHS          (SEQ ID NO 56)

VARIABLE REGION VH (2B)

QVQLVQSGAE VMKPGSSVKV SCKASGYTFS YYWLEWVRQA PGHGLEWMGE
IDPGTFTTNY NEKFKARVTF TADTSTSTAY MELSSLRSED TAVYYCARFS
HFSGSNYDYF DYWGQGTLVT VSS          (SEQ ID NO 68)

CONSTANT REGION CH1-3(IgG1) (SEQ ID NO 60)

ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

Figure 10F Polypeptide Sequence of MAb CL-1136-2C

LIGHT CHAIN

SIGNAL PEPTIDE

MEWSGVFMFLLSVTAGVHS          (SEQ ID NO 56)

VARIABLE REGION Vk

EIVMTQSPAT LSVSPGERAT LSCRASQSIG TNIHWYQQKP GQAPRLLIYY
ASESISGIPA RFSGSGSGTE FTLTISSLQS EDFAVYYCQQ SWSWPTTFGG
GTKVEIK          (SEQ ID NO 69)

CONSTANT REGION Ck          (SEQ ID NO 58)

TVAAPSVFIF PPSDEQLKSG TASVVCLLNN FYPREAKVQW KVDNALQSGN
SQESVTEQDS KDSTYSLSST LTLSKADYEK HKVYACEVTH QGLSSPVTKS
FNRGEC

HEAVY CHAIN (IgG1)

SIGNAL PEPTIDE

MEWSGVFMFLLSVTAGVHS          (SEQ ID NO 56)

VARIABLE REGION (VH)

QVQLVQSGAE VKKPGSSVKV SCKASGYTFS WYWLEWVRQA PGQGLEWMGE
ISPGTFTTNY NEKFKARVTF TADTSTSTAY MELSSLRSED TAVYYCARFS
HFSGSNYDYF DYWGQGTLVT VSS          (SEQ ID NO 70)

CONSTANT REGION CH1-3(IgG1)          (SEQ ID NO 60)

ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCP PCPAPELLGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

HIGH AFFINITY, ANTI-HUMAN IGE ANTIBODIES

This application is a divisional of U.S. application Ser. No. 13/559,938, filed Jul. 27, 2012, now U.S. Pat. No. 8,604,171, which is a continuation of U.S. application Ser. No. 12/413,014, filed Mar. 27, 2009, now, U.S. Pat. No. 8,252,284, which is a continuation of U.S. application Ser. No. 10/544,056, filed Apr. 19, 2006, now U.S. Pat. No. 7,531,169, which claims and is entitled to priority benefit of International Application No. PCT/US2004/002894, filed Feb. 2, 2004 and U.S. Provisional Application No. 60/444,229, filed Feb. 1, 2003, all of which are incorporated herein by reference in their entirety.

BACKGROUND OF THE INVENTION

Allergy is a hypersensitive state induced by an exaggerated immune response to a foreign agent, such as an allergen. Immediate (type I) hypersensitivity, characterized by allergic reactions immediately following contact with the allergen, is mediated via B cells and is based on antigen-antibody reactions. Delayed hypersensitivity is mediated via T cells and based on mechanisms of cellular immunity. In recent years, the term "allergy" has become more and more synonymous with type I hypersensitivity.

Immediate hypersensitivity is a response based on the production of antibodies of the immunoglobulin class E (IgE antibodies) by B cells which upon exposure to an allergen differentiate into antibody secreting plasma cells. The IgE induced reaction is a local event occurring at the site of the allergen's entry into the body, i.e. at mucosal surfaces and/or at local lymph nodes. Locally produced IgE will first sensitize local mast cells, i.e. IgE antibodies bind with their constant regions to Fcε receptors on the surface of the mast cells, and then "spill-over" IgE enters the circulation and binds to receptors on both circulating basophils and tissue-fixed mast cells throughout the body. When the bound IgE is subsequently contacted with the allergen, the Fcε receptors are crosslinked by binding of the allergen causing the cells to degranulate and release a number of anaphylactic mediators such as histamine, prostaglandins, leukotrienes, etc. It is the release of these substances which is responsible for the clinical symptoms typical of immediate hypersensitivity, namely contraction of smooth muscle in the respiratory tract or the intestine, the dilation of small blood vessels and the increase in their permeability to water and plasma proteins, the secretion of mucus resulting, e.g in allergic rhinitis, atopic excema and asthma, and the stimulation of nerve endings in the skin resulting in itching and pain. In addition, the reaction upon second contact with the allergen is intensified because some B cells form a "memory pool" of surface IgE positive B cells (sIgE$^+$ B cells) after the first contact with the allergen by expressing IgE on the cell surface.

There are two major receptors for IgE, the high affinity receptor FcεRI and the low-affinity receptor FcεRII. FcεRI is predominantly expressed on the surface of mast cells and basophils, but low levels of FcεRI can also be found on human Langerhan's cells, dendritic cells, and monocytes, where it functions in IgE-mediated allergen presentation. In addition, FcεRI has been reported on human eosinophils and platelets (Hasegawa, S. et. al., *Hematopoiesis*, 1999, 93:2543-2551). FcεRI is not found on the surface of B cells, T cells, or neutrophils. The expression of FcεRI on Langerhan's cells and dermal dendritic cells is functionally and biologically important for IgE-bound antigen presentation in allergic individuals (Klubal R. et al., *J. Invest. Dermatol.* 1997, 108 (3): 336-42).

The low-affinity receptor, FcεRII (CD23) is a lectin-like molecule comprising three identical subunits with head structures extending from a long α-helical coiled stalk from the cellular plasma membrane (Dierks, A. E. et al., *J. Immunol.* 1993, 150:2372-2382). Upon binding to IgE, FcεRII associates with CD21 on B cells involved in the regulation of synthesis of IgE (Sanon, A. et al., *J. Allergy Clin. Immunol.* 1990, 86:333-344, Bonnefoy, J. et al., *Eur. Resp. J.* 1996, 9:63s-66s). FcεRII has long been recognized for allergen presentation (Sutton and Gould, 1993, *Nature*, 366:421-428). IgE bound to FcεRII on epithelial cells is responsible for specific and rapid allergen presentation (Yang, P. P., *J. Clin. Invest.*, 2000, 106:879-886). FcεRII is present on several cell types, including B-cells, eosinophils, platelets, natural killer cells, T-cells, follicular dendritic cells, and Langerhan's cells.

The structural entities on the IgE molecule that interact with FcεRI and FcεRII have also been identified. Mutagenesis studies have indicated that the CH3 domain mediates IgE interaction with both FcεRI (Presta et al., *J. Biol. Chem.* 1994, 269:26368-26373; Henry A. J. et al., *Biochemistry*, 1997, 36:15568-15578) and FcεRII (Sutton and Gould, *Nature*, 1993, 366: 421-428; Shi, J. et al., *Biochemistry*, 1997, 36:2112-2122). The binding sites for both high- and low-affinity receptors are located symmetrically along a central rotational axis through the two CH3 domains. The FcεRI-binding site is located in a CH3 domain on the outward side near the junction of the CH2 domain, whereas the FcεRII-binding site is on the carboxyl-terminus of CH3.

A promising concept for the treatment of allergy involves the application of monoclonal antibodies, which are IgE isotype-specific and are thus capable of binding IgE. This approach is based on the inhibition of allergic reactions by downregulating the IgE immune response, which is the earliest event in the induction of allergy and provides for the maintenance of the allergic state. As the response of other antibody classes is not affected, both an immediate and a long lasting effect on allergic symptoms is achieved. Early studies of human basophil density showed a correlation between the level of IgE in the plasma of a patient and the number of FcεRI receptors per basophil (Malveaux et al., *J. Clin. Invest.*, 1978, 62:176). They noted that the FcεRI densities in allergic and non-allergic persons range from $10^4$ to $10^6$ receptors per basophil. Later it was shown that treatment of allergic diseases with anti-IgE decreased the amount of circulating IgE to 1% of pretreatment levels (MacGlashan et al., *J. Immunol.*, 1997, 158:1438-1445). MacGlashan analyzed serum obtained from patients treated with whole anti-IgE antibody, which binds free IgE circulating in the serum of the patient. They reported that lowering the level of circulating IgE in a patient resulted in a lower number of receptors present on the surface of basophils. Thus, they hypothesized that FcεRI density on the surface of basophils and mast cells is directly or indirectly regulated by the level of circulating IgE antibody.

More recently, WO 99/62550 disclosed the use of IgE molecules and fragments, which bind to FcεRI and FcεRII IgE binding sites to block IgE binding to receptors. However, effective therapies that lack deleterious side effects for the management of these allergic diseases are limited. One therapeutic approach to treating allergic diseases involved using humanized anti-IgE antibody to treat allergic rhinitis and asthma (Corne, J. et al., *J. Clin. Invest.* 1997, 99:879-887; Racine-Poon, A. et al., *Clin. Pharmcol. Ther.* 1997, 62:675-690; Fahy, J. V. et al., *Am. J. Resp. Crit. Care Med.* 1997, 155:1824-1834; Boulet, L. P. et al., *Am. J. Resp. Crit. Care*

Med., 1997, 155:1835-1840; Milgrom, E. et al., *N. Engl. J. Med.*, 1999, 341:1966-1973). These clinical data demonstrate that inhibition of IgE binding to its receptors is an effective approach to treating allergic diseases.

Antibodies suitable as anti-allergic agents should react with surface IgE positive B cells which differentiate into IgE producing plasma cells, so that they can be used to functionally eliminate those B cells. However, antibodies to IgE in principle may also induce mediator release from IgE sensitized mast cells by crosslinking the Fcε receptors, thus antagonizing the beneficial effect exerted on the serum IgE and sIgE$^+$ B cell level. Therefore, antibodies applicable for therapy of allergy must not be capable of reacting with IgE bound on sensitized mast cells and basophils, but should retain the capability to recognize sIgE$^+$ B cells.

Such IgE isotype-specific antibodies have been described e.g. by Chang et al. (Biotechnology 8, 122-126 (1990)), in European Patent No. EPO407392, and several U.S. patents, e.g., U.S. Pat. No. 5,449,760. However, as the disclosed antibodies are not of human origin they are less suitable for application to humans due to their immunogenicity as foreign proteins. This drawback may potentially be reduced by transforming, e.g., a rodent anti-IgE monoclonal antibody into a chimeric antibody which combines the variable domains of the rodent antibody with human antibody constant domains. This approach conserves the antigen-binding site of the rodent parent anti-IgE antibody, while conferring the human isotype and effector functions. The immunogenicity of a chimeric antibody can be further reduced by grafting rodent hypervariable regions, also termed complementarity determining regions (CDRs), into the frameworks of human light and heavy chain variable region domains resulting in reshaped human antibodies. The technique involves the substitution or recombinant grafting of antigen-specific rodent CDR sequences for those existent within "generic" human heavy and light chain variable domains (U.S. Pat. No. 6,180, 370).

Natural intact immunoglobulins or antibodies comprise a generally Y-shaped tetrameric molecule having an antigen binding-site at the end of each upper arm. An antigen binding site consists of the variable domain of a heavy chain associated with the variable domain of a light chain. More specifically, the antigen binding site of an antibody is essentially formed by the 3 CDRs of the variable domain of a heavy chain ($V_H$) and the 3 CDRs of the variable domain of the light chain ($V_L$). In both $V_L$ and $V_H$ the CDRs alternate with 4 framework regions (FRs) forming a polypeptide chain of the general formula

FR1-CDR1-FR2-CDR2-FR3-CDR3-FR4  (I), wherein the polypeptide chain is described as starting at the N-terminal extremity and ending at the C-terminal extremity. The CDRs of $V_H$ and $V_L$ are also referred to as H1, H2, H3, and L1, L2, L3, respectively. The determination as to what constitutes an FR or a CDR is usually made by comparing the amino acid sequences of a number of antibodies raised in the same species and general rules for identification are known in the art ("Sequences of proteins of immunological interest", Kabat E. A. et al., US department of health and human service, Public health service, National Institute of Health).

The contribution made by a light chain variable domain to the energetics of binding is small as compared with that made by the associated heavy chain variable domain, and isolated heavy chain variable domains have an antigen binding activity on their own. Such molecules are commonly referred to as single domain antibodies (Ward, E. S. et al., Nature 341, 544-546 (1989)).

The CDRs form loops which, within the domains, are connected to a β-sheet framework. The relationship between amino acid sequence and structure of a loop can be described by a canonical structure model (Chothia et al., Nature 342, 887-883 (1989)). According to this model, antibodies have only a few main-chain conformations or "canonical structures" for each hypervariable region. The conformations are determined by the presence of a few key amino acid residues at specific sites in the CDRs and, for certain loops, in the framework regions. Hypervariable regions that have the same conformations in different immunoglobulins have the same or very similar amino acid residues at these sites.

CDR grafting has been carried out for monoclonal antibodies yielding humanized human antibodies with a binding affinity significantly lower than that of the rodent CDR-donor antibody. Findings have indicated that, in addition to the transfer of CDRs, changes within the framework of the human sequence may be necessary in some instances to provide satisfactory antigen binding activity in the CDR-grafted product.

Queen et al. (Proc. Natl. Acad. Sci. USA 86, 10029-10033 (1989)) disclosed that the CDRs from a murine anti-Tac monoclonal antibody could be grafted into a human framework. The human frameworks were chosen to maximize homology with the murine sequence. The authors used a computer model of the murine parent antibody to identify amino acid residues located within the FRs that are close enough to interact with the CDRs or antigen. These residues were mutated to the residue found in the murine sequence. The humanized anti-Tac antibody had an affinity that was only about ⅓ that of the murine anti-Tac antibody and maintenance of the human character of this antibody was problematic.

Treatment of diseases with very high levels of IgE may require an antibody with higher affinity to reduce the risk of immunogenicity, and to expand the clinical indications to diseases with very high levels of IgE, e.g., atopic dermatitis. Thus, it is desirable to have an anti-IgE antibody with greater level of humanization and much higher affinity for IgE. The antibodies in this invention are anti-human IgE antibodies with ultra high affinities and a higher degree of human sequence homology lowering the risk of immunogenicity.

Thus, there is a need for higher affinity humanized antibodies that will allow lowering the amount of antibody necessary to treat disease, thereby lowering the potential side-effects from immunogenicity of the drug and the cost to the patient. Morover, the present invention improves the probability that high affinity antibodies will be identified.

SUMMARY OF THE INVENTION

The present invention relates to high affinity antibodies generated from a parent antibody, particularly very high affinity anti-IgE antibodies. These high affinity antibodies bind the target epitope with at least 20 fold greater binding affinity than the original parent antibody, with increases in affinity ranging from about 100 fold to about 5000 fold greater affinity.

The present invention is also directed to a method of making such high affinity antibodies from a parent antibody molecule, combining the humanization and affinity maturation of a non-human antibody in a rapid and efficient method that increases binding affinity significantly over other methods. This method involves the simultaneous or sequential modification of the CDRs and framework regions of the parent antibody molecule by generating a library of randomly substituted CDRs and/or framework regions, and screening for high affinity molecules.

One embodiment of the present invention

BRIEF DESCRIPTION OF THE FIGURES

FIG. 3A depicts the comparison of the light chains of the murine anti-IgE antibody TES-C21 and the combined human template of L16 and JK4.

FIG. 3B depicts the comparison of the heavy chains of TES-C21 and the combined human template DP88 and JH4b.

FIG. 4 presents a table of the framework residue variants having high affinity as compared to the parent TES-C21.

FIGS. 5A and B depict the ELISA titration curves for clones 4, 49, 72, 78, and 136, as compared to the parent Fab of TES-C21 and negative control (5D12).

FIG. 6 depicts an inhibition assay of clones 2C, 5A, and 5I, as compared to the parent TES-C21 and a negative control antibody.

FIG. 7 depicts the sequences of clones having a combination of beneficial mutations which resulted in even greater affinity for IgE.

FIGS. 8A & 8B depict the framework sequences of the entire light chain variable region for clones 136, 1, 2, 4, 8, 13, 15, 21, 30, 31, 35, 43, 44, 53, 81, 90, and 113.

FIGS. 9A & 9B depict the framework sequences of the entire heavy chain variable region for 35 clones.

FIGS. 10 A-F depict the complete heavy and light chain sequences for clones 136, 2C, 5I, 5A, 2B, and 1136-2C.

DETAILED DESCRIPTION OF THE INVENTION

Definitions

Figure 1:
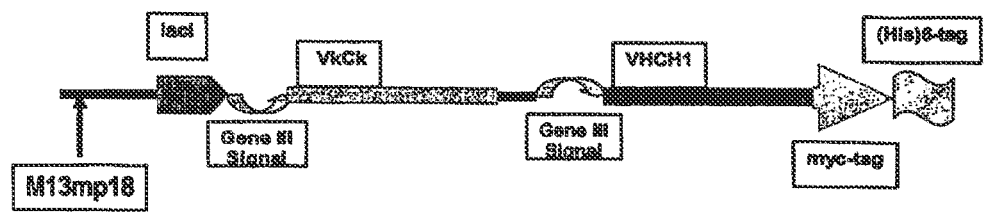
FIG. 1 is a schematic representation of the phage vector used in antibody cloning and screening.

Terms used throughout this application are to be construed with ordinary and typical meaning to those of ordinary skill in the art. However, Applicants desire that the following terms be given the particular definition as defined below.

The phrase "substantially identical" with respect to an antibody chain polypeptide sequence may be construed as an antibody chain exhibiting at least 70%, or 80%, or 90% or 95% sequence identity to the reference polypeptide sequence. The term with respect to a nucleic acid sequence may be construed as a sequence of nucleotides exhibiting at least about 85%, or 90%, or 95% or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

As used herein, "anti-human IgE antibody" means an antibody which binds to human IgE in such a manner so as to inhibit or substantially reduce the binding of such IgE to the high affinity receptor, FcεRI.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs) also known as hypervariable regions both in the light chain and the heavy chain variable domains. The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat et al.) As used herein, numbering of immunoglobulin amino acid residues is done according to the immunoglobulin amino acid residue numbering system of Kabat et al., (Sequences of Proteins of Immunological Interest, National Institute of Health, Bethesda, Md. 1987), unless otherwise indicated.

The term "antibody fragment" refers to a portion of a full-length antibody, generally the target binding or variable region. Examples of antibody fragments include Fab, Fab', $F(ab')_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI. As used herein, "functional fragment" with respect to antibodies, refers to Fv, F(ab) and $F(ab')_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define an target binding site on the surface of the $V_H$-$V_L$ dimer. Collectively, the six CDRs confer target binding specificity to the antibody. However, even a single variable domain (or half of an Fv comprising only three CDRs specific for an target) has the ability to recognize and bind target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single targetic site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well known techniques. The parent monoclonal antibodies to be used in accordance with the present invention may be made by the hybridoma method first described by Kohler and Milstein, Nature 256, 495 (1975), or may be made by recombinant methods.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

The terms "cell", "cell line" and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

"Transformation" of a cellular organism with DNA means introducing DNA into an organism so that the DNA is replicable, either as an extrachromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of E. coli. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The term "vector" means a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control the termination of transcription and translation. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. DNA for a presequence or secretory leader may be operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

"Mammal" for purposes of treatment refers to any animal classified as a mammal, including human, domestic and farm animals, nonhuman primates, and zoo, sports, or pet animals, such as dogs, horses, cats, cows, etc.

The term "epitope tagged" when used herein in the context of a polypeptide refers to a polypeptide fused to an "epitope tag". The epitope tag polypeptide has enough residues to provide an epitope against which an antibody can be made, yet is short enough such that it does not interfere with activity of the polypeptide. The epitope tag preferably also is fairly unique so that the antibody does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al, Mol. Cell. Biol. 8: 2159-2165 (1988))); the c-myc tag and the 8F9, 3C7, 6E10, G4, B7 and 9E10 antibodies thereagainst (Evan et al., Mol. Cell. Biol. 5(12): 3610-3616 (1985)); and the Herpes Simplex virus glycoprotein D (gD) tag and its antibody (Paborsky et al., Protein Engineering 3(6): 547-553 (1990)). In certain embodiments, the epitope tag may be an epitope of the Fc region of an IgG molecule (e.g., IgG1, IgG2, IgG3 or IgG4) that is responsible for increasing the in vivo serum half-life of the IgG molecule.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Example of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column).

As used herein, the term "IgE-mediated disorder" means a condition or disease which is characterized by the overproduction and/or hypersensitivity to the immunoglobulin IgE. Specifically it would be construed to include conditions associated with anaphylactic hypersensitivity and atopic allergies, including for example: asthma, allergic rhinitis & conjunctivitis (hay fever), eczema, urticaria, atopic dermatitis, and food allergies. The serious physiological condition of anaphylactic shock caused by, e.g., bee stings, snake bites, food or medication, is also encompassed under the scope of this term.

Generation of Antibodies

The starting or "parent" antibody may be prepared using techniques available in the art for generating such antibodies. These techniques are well known. Exemplary methods for generating the starting antibody are described in more detail in the following sections. These descriptions are possible alternatives for making or selecting a parent antibody and in no way limit the methods by which such a molecule may be generated.

The antibody's binding affinity is determined prior to generating a high affinity antibody of the present invention. Also, the antibody may be subjected to other biological activity assays, e.g., in order to evaluate effectiveness as a therapeutic. Such assays are known in the art and depend on the target target and intended use for the antibody.

To screen for antibodies which bind to a particular epitope (e.g., those which block binding of IgE to its high affinity receptor), a routine cross-blocking assay such as that described in "Antibodies: A Laboratory Manual" (Cold Spring Harbor Laboratory, Ed Harlow and David Lane (1988)) can be performed. Alternatively, epitope mapping can be performed to determine where the antibody binds an epitope of interest. Optionally, the binding affinity of the antibody for a homolog of the target used to generate the antibody (where the homolog is from a different species) may be assessed using techniques known in the art. In one embodiment, the other species is a nonhuman mammal to which the antibody will be administered in preclinical studies. Accordingly, the species may be a nonhuman primate, such as rhesus, cynomolgus, baboon, chimpanzee and macaque. In other embodiments, the species may be a rodent, cat or dog, for example.

The parent antibody is altered according to the present invention so as to generate an antibody which has a higher or stronger binding affinity for the target than the parent antibody. The resulting high affinity antibody preferably has a binding affinity for the target which is at least about 10 fold higher, or at least about 20 fold higher, or at least about 500 fold higher or may be 1000 to 5000 fold higher, than the binding affinity of the parent antibody for the target. The degree of enhancement in binding affinity necessary or desired will depend on the initial binding affinity of the parent antibody.

In general, the method for making high affinity antibodies from a parent antibody involves the following steps:

1. Obtaining or selecting a parent antibody which binds the target of interest, which comprises heavy and light chain variable domains. This may be done by traditional hybridoma techniques, phage-display techniques, or any other method of generating a target specific antibody.

2. Selecting a framework sequence which is close in sequence to the parent framework, preferably a human template sequence. This template may be chosen based on, e.g., its comparative overall length, the size of the CDRs, the amino acid residues located at the junction between the framework and the CDRs, overall homology, etc. The template chosen can be a mixture of more than one sequence or may be a consensus template.

3. Generating a library of clones by making random amino acid substitutions at each and every possible CDR position. One may also randomly substitute the amino acids in the human framework template that are, e.g., adjacent to the CDRs or that may affect binding or folding, with all possible amino acids, generating a library of framework substitutions. These framework substitutions can be assessed for their potential effect on target binding and antibody folding. The substitution of amino acids in the framework may be done either simultaneously or sequentially with the substitution of the amino acids in the CDRs. One method for generating the library of variants by oligonucleotide synthesis.

4. Constructing an expression vector comprising the heavy and/or light chain variants generated in step (3) which may comprise the formulas: FRH1-CDRH1-FRH2-CDRH2-FRH3-CDRH3-FRH4(I) and FRL1-CDRL1-FRL2-CDRL2-FRL3-CDRL3-FRL4 (II), wherein FRL1, FRL2, FRL3, FRL4, FRH1, FRH2, FRH3 and FRH4 represent the variants of the framework template light chain and heavy chain sequences chosen in step 3 and the CDRs represent the variant CDRs of the parent antibody CDRs. An example of a vector containing such light and heavy chain sequences is depicted in FIG. 1.

5. Screening the library of clones against the specific target and those clones that bind the target are screened for improved binding affinity. Those clones that bind with greater affinity than the parent molecule may be selected. The optimal high affinity candidate will have the greatest binding affinity possible compared to the parent antibody, preferably greater then 20 fold, 100 fold, 1000 fold or 5000 fold. If the chosen variant contains certain amino acids that are undesirable, such as a glycosylation site that has been introduced or a potentially immunogenic site, those amino acids may be replaced with more beneficial amino acid residues and the binding affinity reassessed.

One may also use this method to generate high affinity antibodies from a fully human parent antibody by randomly substituting only the CDR regions, leaving the human framework intact.

Due to improved high throughput screening techniques and vectors such as the one depicted in FIG. 1, an artisan can rapidly and efficiently screen a comprehensive library of substitutions at all sites in a given CDR and/or framework region. By randomly substituting all amino acids at all positions simultaneously, one is able to screen possible combinations that significantly increase affinity that would not have been anticipated or identified by individual substitution due to, e.g., synergy.

Parent Antibody Preparation

A. Target Preparation

Soluble targets or fragments thereof can be used as immunogens for generating antibodies. The antibody is directed against the target of interest. Preferably, the target is a biologically important polypeptide and administration of the antibody to a mammal suffering from a disease or disorder can result in a therapeutic benefit in that mammal. However, antibodies may be directed against nonpolypeptide targets. Where the target is a polypeptide, it may be a transmembrane molecule (e.g. receptor) or ligand such as a growth factor. One target of the present invention is IgE. Whole cells may be used as the immunogen for making antibodies. The target may be produced recombinantly or made using synthetic methods. The target may also be isolated from a natural source.

For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. mast cell lines) or may be cells which have been transformed by recombinant techniques to express the transmembrane molecule. Other targets and forms thereof useful for preparing antibodies will be apparent to those in the art.

B. Polyclonal Antibodies

Polyclonal antibodies are usually generated in non-human mammals by multiple subcutaneous (sc) or intraperitoneal (ip) injections of the relevant target in combination with an adjuvant. It may be useful to conjugate the relevant target to a protein that is immunogenic in the species to be immunized, e.g., keyhole limpet hemocyanin. Numerous agents capable of eliciting an immunological response are well known in the art.

Animals are immunized against the target, immunogenic conjugates, or derivatives by combining the protein or conjugate (for rabbits or mice, respectively) with Freund's complete adjuvant and injecting the solution intradermally. One month later the animals are boosted with ⅕ to ⅒ the original amount of peptide or conjugate in Freund's incomplete adjuvant by subcutaneous injection at multiple sites. Seven to 14 days later the animals are bled and the serum is assayed for antibody titer. Animals are boosted until the titer plateaus.

The mammalian antibody selected will normally have a sufficiently strong binding affinity for the target. For example, the antibody may bind the human anti-IgE target with a binding affinity (Kd) value of about $1 \times 10^{-8}$ M. Antibody affinities may be determined by saturation binding; enzyme-linked immunoabsorbant assay (ELISA); and competition assays (e.g., radioimmunoassays).

To screen for antibodies that bind the target of interest, a routine crosslinking assay such as that described in Antibodies, A Laboratory Manual, Cold Spring Harbor Laboratory, Ed Harlow and David Lane (1988) can be performed. Alternatively, epitope mapping, e.g., as described in Champe, et al. J. Biol. Chem. 270: 1388-1394 (1995), can be performed to determine binding.

C. Monoclonal Antibodies

Monoclonal antibodies are antibodies which recognize a single antigenic site. Their uniform specificity makes monoclonal antibodies much more useful than polyclonal antibodies, which usually contain antibodies that recognize a variety of different antigenic sites. Monoclonal antibodies may be made using the hybridoma method first described by Kohler et al., Nature, 256: 495 (1975), or may be made by recombinant DNA methods.

In the hybridoma method, a mouse or other appropriate host animal, such as a rodent, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principals and Practice, pp. 590-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), substances which prevent the growth of HGPRT-deficient cells. Preferred myeloma cells are those that fuse efficiently, support stable high-level production of antibody by the selected antibody-producing cells, and are sensitive to a medium such as HAT medium. Human myeloma and mouse-human heteromyeloma cell lines have been described for the production of human monoclonal antibodies (Kozbar, J. Immunol. 133: 3001 (1984); Brodeur et al., Monoclonal Antibody Production Techniques and Applications, pp. 51-63 (Marcel Dekker, Inc., New York, 1987)).

After hybridoma cells are identified that produce antibodies of the desired specificity, affinity, and/or activity, the clones may be subcloned by limiting dilution procedures and grown by standard methods (Goding, Monoclonal Antibodies: Principals and Practice, pp. 59-103, Academic Press, 1986)). Suitable culture media for this purpose include. The monoclonal antibodies secreted by the subclones are suitably separated from the culture medium by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transferred into host cells such as E. coli cells, NS0 cells, Chinese hamster ovary (CHO) cells, or myeloma cells to obtain the synthesis of monoclonal antibodies in the recombinant host cells. The DNA also may be modified, for example, by substituting the coding sequence for human heavy- and light-chain constant domains in place of the homologous murine sequences (U.S. Pat. No. 4,816,567; Morrison et al., Proc. Natl. Acad. Sci. USA 81: 6851 (1984)), or by covalently joining to the immunoglobulin polypeptide.

D. Humanized Antibodies

Humanization is a technique for making a chimeric antibody wherein substantially less than an intact human variable domain has been substituted by the corresponding sequence from a non-human species. A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al, Nature 321: 522-525 (1986); Riechman et al., Nature 332: 323-327 (1988); Verhoeyens et al., Science 239: 1534-1536 (1988)), by substituting non-human CDR's or CDR sequences for the corresponding sequences in a human antibody (See, e.g., U.S. Pat. No. 4,816,567). As practiced in the present invention, the humanized antibody may have some CDR residues and some FR residues substituted by residues from analogous sites in murine antibodies.

The choice of human variable domains, both light and heavy, to be used in making the humanized antibodies is very important to reduce antigenicity. According to the so-called "best fit" method, the sequence of the variable domain of a non-human antibody is compared with the library of known human variable-domain sequences. The human sequence which is closest to that of the non-human parent antibody is then accepted as the human framework for the humanized antibody (Sims et al., J. Immunol. 151: 2296 (1993); Chothia et al., J. Mol. Biol. 196: 901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol. 151: 2623 (1993)).

E. Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science 229: 81 (1985)). However, these fragments can now be produced directly by recombinant host cells. For example, the antibody fragments can be isolated from an antibody phage library. Alternatively, F(ab')$_2$—SH fragments can be directly recovered from *E. coli* and chemically coupled to form F(ab')$_2$ fragments (Carter et al., Bio/Technology 10: 163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). (PCT patent application WO 93/16185).

Preparation of High Affinity Antibodies

Once the parent antibody has been identified and isolated, one or more amino acid residues are altered in one or more of the variable regions of the parent antibody. Alternatively, or in addition, one or more substitutions of framework residues may be introduced in the parent antibody where these result in an improvement in the binding affinity of the antibody, for example, for human IgE. Examples of framework region residues to modify include those which non-covalently bind target directly (Amit et al. Science 233: 747-753 (1986)); interact with/effect the conformation of CDR (Chothia et al. J. Mol. Biol. 196: 901-917 (1987)); and/or participate in the VL-VH interface (EP 239 400 B1). In certain embodiments, modification of one or more of such framework region residues results in an enhancement of the binding affinity of the antibody for the target of interest.

Modifications in the antibodies' biological properties may be accomplished by selecting substitutions that differ significantly in their effect on maintaining, e.g., (a) the structure of the polypeptide backbone in the area of the substitution, for example, as a sheet or helical conformation; (b) the charge or hydrophobicity of the molecule at the target site, or (c) the bulk of the side chain. Non-conservative substitutions will entail exchanging a member of one of these classes for another class.

Nucleic acid molecules encoding amino acid sequence variants are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the species-dependent antibody. The preferred method for generating variants is an oligonucleotide-mediated synthesis. In certain embodiments, the antibody variant will only have a single hypervariable region residue substituted, e.g. from about two to about fifteen hypervariable region substitutions.

Figure 2:
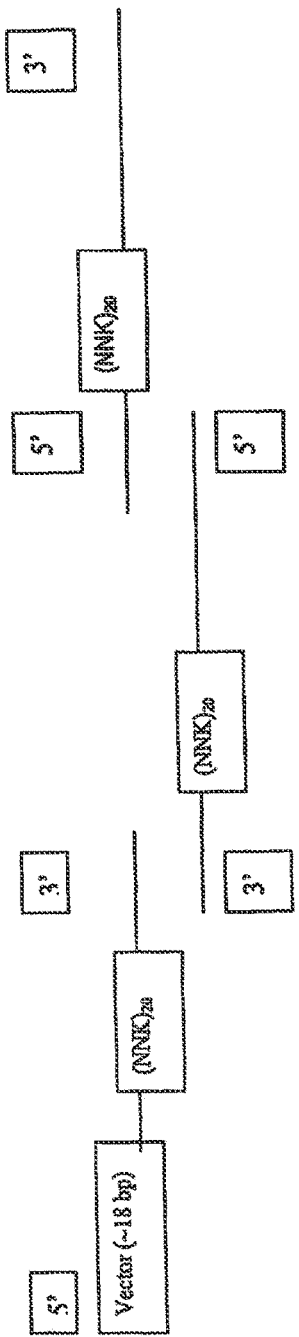
FIG. 2 is a schematic representation of oligonucleotides useful in generating antibody variants.

One method for generating the library of variants is by oligonucleotide mediated synthesis according to the scheme depicted in FIG. 2. Three oligonucleotides of approximately 100 nucleotides each may be synthesized spanning the entire light chain or heavy chain variable region. Each oligonucleotide may comprise: (1) a 60 amino acid stretch generated by the triplet (NNK)$_{20}$ where N is any nucleotide and K is G or T, and (2) an approximately 15-30 nucleotide overlap with either the next oligo or with the vector sequence at each end. Upon annealing of these three oligonucleotides in a PCR reaction, the polymerase will fill in the opposite strand generating a complete double stranded heavy chain or light chain variable region sequence. The number of triplets may be adjusted to any length of repeats and their position within the oligonucleotide may be chosen so as to only substitute amino acds in a given CDR or framework region. By using (NNK), all twenty amino acids are possible at each position in the encoded variants. The overlapping sequence of 5-10 amino acids (15-30 nucloetides) will not be substituted, but this may be chosen to fall within the stacking regions of the framework, or may substituted by a separate or subsequent round of synthesis. Methods for synthesizing oligonucleotides are well known in the art and are also commercially available. Methods for generating the antibody variants from these oligonucleotides are also well known in the art, e.g., PCR.

The library of heavy and light chain variants, differing at random positions in their sequence, can be constructed in a any expression vector, such as a bacteriophage, specifically the vector of FIG. 1, each of which contains DNA encoding a particular heavy and light chain variant.

Following production of the antibody variants, the biological activity of variant relative to the parent antibody is determined. As noted above, this involves determining the binding affinity of the variant for the target. Numerous high-throughput methods exist for rapidly screen antibody variants for their ability to bind the target of interest.

One or more of the antibody variants selected from this initial screen may then be screened for enhanced binding affinity relative to the parent antibody. One common method for determining binding affinity is by assessing the association and dissociation rate constants using a BIAcore™ surface plasmon resonance system (BIAcore, Inc.). A biosensor chip is activated for covalent coupling of the target according to the manufacturer's (BIAcore) instructions. The target is then diluted and injected over the chip to obtain a signal in response units (RU) of immobilized material. Since the signal in RU is proportional to the mass of immobilized material, this represents a range of immobilized target densities on the matrix. Dissociation data are fit to a one-site model to obtain koff+/−s.d. (standard deviation of measurements). Pseudo-first order rate constant (ks) are calculated for each association curve, and plotted as a function of protein concentration to obtain kon+/−s.e. (standard error of fit). Equilibrium dissociation constants for binding, Kd's, are calculated from SPR measurements as koff/kon. Since the equilibrium dissociation constant, Kd, is inversely proportional to koff, an estimate of affinity improvement can be made assuming the association rate (kon) is a constant for all variants.

The resulting candidate(s) with high affinity may optionally be subjected to one or more further biological activity assays to confirm that the antibody variant(s) with enhanced binding affinity still retain the desired therapeutic attributes. For example, in the case of an anti-IgE antibody, one may screen for those that block binding of IgE to its receptor and inhibit the release of histamine. The optimal antibody variant retains the ability to bind the target with a binding affinity significantly higher than the parent antibody.

The antibody variant(s) so selected may be subjected to further modifications oftentimes depending upon the intended use of the antibody. Such modifications may involve further alteration of the amino acid sequence, fusion to heterologous polypeptide(s) and/or covalent modifications such as those elaborated below. For example, any cysteines residues not involved in maintaining the proper conformation of the antibody variant may be substituted, generally with serine, to improve the oxidative stability of the molecule and prevent aberrant cross linking. Conversely, (a) cysteine bond(s) may be added to the antibody to improve its stability (particularly where the antibody is an antibody fragment such as an Fv fragment).

Vectors

The invention also provides isolated nucleic acid encoding an antibody variant as disclosed herein, vectors and host cells comprising the nucleic acid, and recombinant techniques for the production of the antibody variant. For recombinant production of the antibody variant, the nucleic acid encoding it is isolated and inserted into a replicable vector for further cloning (amplification of the DNA) or for expression. DNA encoding the antibody variant is readily isolated and sequenced using conventional procedures (e.g., by using oligonucleotide probes that are capable of binding specifically to genes encoding the heavy and light chains of the antibody variant).

Many vectors are available. The vector components generally include, but are not limited to, one or more of the following: a signal sequence, an origin of replication, one or more marker genes, an enhancer element, a promoter, and a transcription termination sequence.

The phage expression vector depicted in FIG. 1 is comprised of a commonly used M13 vector and M13's own gene III viral secretion signal for rapid secretion and screening variant Fabs for proper binding specificity and minimal affinity criteria. This vector does not use the entire gene III sequence, so there is no display on the surface of the bacterial cell, but rather the Fabs are secreted into the periplasmic space. Alternatively, the Fabs could be expressed in the cytoplasm and isolated. The heavy and light chains each have their own viral secretion signal, but are dependently expressed from a single strong inducible promoter.

The vector in FIG. 1 also provides a His tag and a myc tag for easy purification, as well as detection. A skilled artisan would recognize that the Fabs could be independently expressed from separate promoters or that the secretion signal need not be the viral sequence chosen, but could be a prokaryotic or eukaryotic signal sequence suitable for the secretion of the antibody fragments from the chosen host cell. It should also be recognized that the heavy and light chains may reside on different vectors.

A. Signal Sequence Component

The antibody variant of this invention may be produced recombinantly. The variant may also be expressed as a fusion polypeptide fused with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by signal peptidase) by the host cell. For prokaryotic host cells that do not recognize and process the native antibody signal sequence, the signal sequence may be substituted by a prokaryotic signal sequence selected, for example, from the group of the alkaline phosphatase, penicillinase, Ipp, or heat-stable enterotoxin II leaders. Or in the case of the vector of FIG. 1, the signal sequence chosen was a viral signal sequence from gene III. For yeast secretion the native signal sequence may be substituted by, e.g., the yeast invertase leader, α-factor leader (including *Saccharomyces* and *Kluyveromyces* α-factor leaders), or acid phosphatase leader, the *C. albicans* glucoamylase leader, or a signal described in e.g., WO 90/13646. In mammalian cell expression, mammalian signal sequences as well as viral secretory leaders, for example, the herpes simplex gD signal, are available. The DNA for such precursor region is ligated in reading frame to DNA encoding the antibody variant.

B. Origin of Replication Component

Vectors usually contain a nucleic acid sequence that enables the vector to replicate in one or more selected host cells. Generally, this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for vectors in mammalian cells. Generally, the origin of replication component is not needed for mammalian expression vectors (the SV40 origin may typically be used only because it contains the early promoter).

C. Selection Gene Component

Vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contain methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. (U.S. Pat. No. 4,965,199).

A suitable selection gene for use in yeast is the trp1 gene present in the yeast plasmid Yrp7 (Stinchcomb et al., Nature 282: 39 (1979)). The trp1 gene provides a selection marker for a variant strain of yeast lacking the ability to grow in tryptophan, for example, ATCC No. 44076 or PEP4-1. Jones, Genetics 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

D. Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems may also contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promotor sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian virus 40 (SV40), from heterologous mammalian promoters, e.g., the actin promoter or an immunoglobulin promoter, from heat-shock promoters—provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, human β-interferon cDNA has been expressed in mouse cells under the control of a thymidine kinase promoter from herpes simplex virus. Alternatively, the rous sarcoma virus long terminal repeat can be used as the promoter.

E. Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297: 17-18 (1982) on enhancing elements for activation of eukaryotic promoters. The enhancer may be spliced into the vector at a position 5' or 3' to the antibody-encoding sequence, but is preferably located at a site 5' from the promoter.

F. Transcription Termination Component

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See e.g., WO94/11026.

Selection and Transformation of Host Cells

Suitable host cells for cloning or expressing the DNA in the vectors herein are prokaryotic, yeast, or higher eukaryotic cells. Suitable prokaryotes for this purpose include both Gram-negative and Gram-positive organisms, for example, Enterobacteria such as *E. coli, Enterobacter, Erwinia, Klebsiella, Proteus, Salmonella, Serratia*, and *Shigella*, as well as Bacilli, *Pseudomonas*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae* is the most commonly used among lower eukaryotic host microorganisms. However, a number of other genera, species, and strains are commonly available and useful herein, such as *Schizosaccharomyces pombe; Kluyveromyces; Candida; Trichoderma; Neurospora crassa*; and filamentous fungi such as e.g., *Neurospora, Penicillium, Tolypocladium*, and *Aspergillus* hosts, such as *A. nidulans* and *A. niger*.

Suitable host cells for the expression of glycosylated antibodies are derived from multicellular organisms. In principal, any higher eukaryotic cell culture is workable, whether from vertebrate or invertebrate culture. Examples of invertebrate cells include plant and insect cells, Luckow et al., Bio/Technology 6, 47-55 (1988); Miller et al., Genetic Engineering, Setlow et al. eds. Vol. 8, pp. 277-279 (Plenam publishing 1986); Mseda et al., Nature 315, 592-594 (1985). Numerous baculoviral strains and variants and corresponding permissive insect host cells from hosts such as *Spodoptera frugiperda* (caterpillar), *Aedes* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

Vertebrate cells, and propagation of vertebrate cells, in culture (tissue culture) has become a routine procedure. See Tissue Culture, Academic Press, Kruse and Patterson, eds. (1973). Examples of useful mammalian host cell lines are monkey kidney; human embryonic kidney line; baby hamster kidney cells; Chinese hamster ovary cells/–DHFR(CHO, Urlaub et al., Proc. Natl. Acad. Sci. USA 77: 4216 (1980)); mouse sertoli cells; human cervical carcinoma cells (HELA); canine kidney cells; human lung cells; human liver cells; mouse mammary tumor; and NS0 cells.

Host cells are transformed with the above-described vectors for antibody production and cultured in conventional nutrient media modified as appropriate for inducing promoters, selecting transformants, or amplifying the genes encoding the desired sequences.

The host cells used to produce the antibody variant of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing host cells. In addition, any of the media described in Ham et al., Meth. Enzymol. 58: 44 (1979), Barnes et al., Anal. Biochem. 102: 255 (1980), U.S. Pat. No. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as GENTAMYCIN™ drug), trace elements (defined as inorganic compounds usually present at finalconcentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Antibody Purification

When using recombinant techniques, the antibody variant can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel elecrophoresis, dialysis, and affinity chromatography, with affinity chromatography being the preferred purification technique. The suitability of protein A as an affinity ligand depends on the species and isotype of any immunoglobulin Fc domain that is present in the antibody variant. Protein A can be used to purify antibodies that are based on human IgG1, IgG2 or IgG4 heavy chains (Lindmark et al., J. Immunol. Meth. 62: 1-13 (1983)). Protein G is recommended for all mouse isotypes and for human IgG3 (Guss et al., EMBO J. 5: 1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody variant comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody variant to be recovered.

Following any preliminary purification step(s), the mixture comprising the antibody variant of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Therapeutic formulations of the polypeptide or antibody may be prepared for storage as lyophilized formulations or aqueous solutions by mixing the polypeptide having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present invention and include polhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, .alpha.-monothioglycerol and sodium thio sulfate; low molecular weight polypeptides (i.e. <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents. The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, A. Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody variant, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

In a preferred embodiment, an aqueous solution of therapeutic polypeptide, antibody or fragment thereof is administered by subcutaneous injection. Each dose may range from about 0.5 µg to about 50 µg per kilogram of body weight, or more preferably, from about 3 µg to about 30 µg per kilogram body weight.

The dosing schedule for subcutaneous administration may vary form once a month to daily depending on a number of clinical factors, including the type of disease, severity of disease, and the subject's sensitivity to the therapeutic agent.
Uses for the Antibody Variant The antibody variants of the invention may be used as affinity purification agents. In this process, the antibodies are immobilized on a solid phase such as SEPHADEX™ resin or filter paper, using methods well known in the art. The immobilized antibody variant is contacted with a sample containing the target to be purified, and thereafter the support is washed with a suitable solvent that will remove substantially all the material in the sample except the target to be purified, which is bound to the immobilized antibody variant. Finally, the support is washed with another suitable solvent, such as glycine buffer, that will release the target from the antibody variant.

The variant antibodies may also be useful in diagnostic assays, e.g., for detecting expression of a target of interest in specific cells, tissues, or serum. For diagnostic applications, the antibody variant typically will be labeled with a detectable moiety. Numerous labels are available Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzym. (Ed. J. Langone & H. Van Vunakis), Academic press, New York, 73: 147-166 (1981).

Sometimes, the label is indirectly conjugated with the antibody variant. The skilled artisan. The skilled artisan will be aware of various techniques for achieving this. For example, the antibody variant can be conjugated with biotin and any of the three broad categories of labels mentioned above can be conjugated with avidin, or vice versa. Biotin binds selectively to avidin and thus, the label can be conjugated with the antibody variant in this indirect manner. Alternatively, to achieve indirect conjugation of the label with the antibody variant, the antibody variant is conjugated with a small hapten (e.g. digloxin) and one of the different types of labels mentioned above is conjugated with an anti-hapten antibody variant (e.g. anti-digloxin antibody). Thus, indirect conjugation of the label with the antibody variant can be achieved.

In another embodiment of the invention, the antibody variant need not be labeled, and the presence thereof can be detected using a labeled antibody which binds to the antibody variant.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample for binding with a limited amount of antibody variant. The amount of target in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, or epitope, or the protein to be detected. In a sandwich assay, the test sample to be analyzed is bound by a first antibody which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody variant is labeled with a radionucleotide (such as .sup.111 In, .sup.99 Tc, .sup.14 C, .sup.131 I, .sup.3 H, sup.32 P or .sup.35 S) so that the tumor can be localized using immunoscintiography. For example, a high affinity anti-IgE antibody of the present invention may be used to detect the amount of IgE present in, e.g., the lungs of an asthmatic patient.

The antibody of the present invention can be provided in a kit, i.e., packaged combination of reagents in predetermined amounts with instructions for performing the diagnostic assay. Where the antibody variant is labeled with an enzyme, the kit may include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

in VIVo Uses for the Antibody

It is contemplated that the antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

The antibody or polypeptide is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

For the prevention or treatment of disease, the appropriate dosage of the antibody or polypeptide will depend on the type of disease to be treated, the severity and course of the disease, whether the antibody variant is administered for preventive or therapeutic purposes, previous therapy, the patient's clinical history and response to the antibody variant, and the discretion of the attending physician. The very high affinity anti-human IgE antibodies of the invention may be suitably administered to the patient at one time or over a series of treatments.

Depending on the type and severity of the disease, about 0.1 mg/kg to 150 mg/kg (e.g., 0.1-20 mg/kg) of antibody is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen for an anti-LFA-1 or anti-ICAM-1 antibody is disclosed in WO 94/04188.

The antibody variant composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody variant to be administered will be governed by such considerations, and is the minimum amount necessary to prevent, ameliorate, or treat a disease or disorder. The antibody variant need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

The antibodies of the present invention which recognize IgE as their target may be used to treat "IgE-mediated disorders". These include diseases such as asthma, allergic rhinitis & conjunctivitis (hay fever), eczema, urticaria, atopic dermatitis, and food allergies. The serious physiological condition of anaphylactic shock caused by, e.g., bee stings, snake bites, food or medication, is also encompassed under the scope of this invention.

EXAMPLES

The following examples are offered by way of illustration and not by way of limitation.

Example 1

Humanization of Anti-IgE Murine MAb TES-C21

The sequences of the heavy chain variable region ($V_H$) and the light chain variable region ($V_L$) of murine mAb TES-C21 were compared with human antibody germline sequences available in the public databases. Several criteria were used when deciding on a template as described in step 1 above, including overall length, similar CDR position within the framework, overall homology, size of the CDR, etc. All of these criteria taken together provided a result for choosing the optimal human template as shown in the sequence alignment between TES-C21 MAb heavy and light chain sequences and the respective human template sequences depicted in FIGS. 3A and 3B.

In this case, more than one human framework template was used to design this antibody. The human template chosen for the $V_H$ chain was a combination of DP88 (aa residues 1-95) and JH4b (aa residues 103-113) (See FIG. 3B). The human template chosen for the $V_L$ chain was a combination of L16 (VK subgroup III, aa residues 1-87) combined with JK4 (aa residues 98-107) (See FIG. 3A). The framework homology between the murine sequence and the human template was about 70% for $V_H$ and about 74% for $V_L$.

Once the template was chosen, a Fab library was constructed by DNA synthesis and overlapping PCR as described above and depicted in FIG. 2. The library was composed of synthesized TES-C21 CDRs synthesized with the respective chosen human templates, DP88/JH4b and L16/JK4. The complexity of the library was 4096 ($=2^{12}$). The overlapping nucleotides encoding partial $V_H$ and $V_L$ sequences were synthesized in the range of about 63 to about 76 nucleotides with 18 to 21 nucleotide overlaps.

PCR amplification of $V_L$ and $V_H$ gene was performed using a biotinylated forward primer containing the specific sequence to the framework region FR1 and an overhanging sequence annealed to the end of leader sequence (GeneIII) and a reverse primer from the conserved constant region (Cκ or CH1) under standard PCR conditions. The PCR product was purified by agarose gel electrophoresis, or by commercial PCR purification kit to remove unincorporated biotinylated primers and non-specific PCR.

5'-Phosphorylation of PCR product was performed using 2 μg PCR product, 1 μL of T4 polynucleotide kinase (10 units/μL), 2 μL of 10×PNK buffer, 1 μL of 10 mM ATP in a total volume of 20 μL adjusted by ddH$_2$O. After incubating at 37° C. for 45 minutes, and heat denaturation at 65° C. for 10 min, the reaction volume was adjusted to 200 μL by adding ddH$_2$O for the next step.

The 100 μL of streptavidin-coated magnetic beads were washed twice with 200 μL 2× B&W buffer and resuspended in 200 μL 2× B&W buffer. The phosphorylated PCR product was mixed with beads, and incubated at room temperature (RT) for 16 min with mild shaking.

The beads were sedimented and washed twice with 200 μL 2× B&W buffer. The non-biotinylated ssDNA (minus strand) was eluted with 300 μL freshly prepared 0.15M NaOH at RT for 10 min with mild shaking. A second NaOH elution can increase the yield slightly (optional). The eluant was centrifuged to remove any trace beads.

The ssDNA was precipitated from the supernatant by adding 1 μL glycogen (10 mg/mL), 1/10 volume of 3M NaOAc (pH 5.2), and 2.5 volumes of EtOH. The precipitated ssDNA was then washed with 70% EtOH followed by lyophilizing for 3 min and dissolving in 20 μL ddH$_2$O. The ssDNA was quantitated by spotting on an ethidium bromide (EtBr) agarose plate with DNA standards, or by measuring OD$_{260}$.

Example 2

Cloning of $V_H$ and $V_L$ into Phage-Expression Vector $V_H$ and $V_L$ were cloned into a phage-expression vector by hybridization mutagenesis. Uridinylated templates were prepared by infecting CJ236 E. coli strain (dut$^-$ ung$^-$) with M13-based phage (phage-expression vector TN003).

The following components [200 ng of uridinylated phage vector (8.49 kb); 92 ng phosphorylated single-stranded H chain (489 bases); 100 ng phosphorylated single-stranded L chain (525 bases); 1 μL 10× annealing buffer; adjust volume with ddH$_2$O to 10 μl] were annealed (at about 8-fold molar ratio of insert to vector) by PCR holding the temperature at 85° C. for 5 min (denaturation) and then ramping to 55° C. over 1 hour. The samples were chilled on ice.

To the annealed product the following components were added: 1.4 μL 10× synthesis buffer; 0.5 μL T4 DNA ligase (1 unit/μL); 1 μL T4 DNA polymerase (1 unit/μL) followed by incubating on ice for 5 min, and 37° C. for 1.5 hours. The product was then ethanol precipitated, and dissolved in 10 μL of ddH$_2$O or TE.

DNA was digested with 1 μL XbaI (10 unit/μL) for 2 h, and heat inactivated at 65° C. for 20 min. Digested DNA was transfected into 50 μL of electro-competent DH10B cells by electroporation. The resulting phage were titered by growing on XL-1 Blue bacterial lawn at 37° C. overnight. Clones were sequenced to confirm composition.

Example 3

Deep Well Culture for Library Screening

A. Plating Phage Library

The phage library was diluted in LB media to achieve the desired number of plaques per plate. High titer phage were mixed with 200 μL XL-1B cell culture. 3 mL LB top agar was mixed, poured onto an LB plate, and allowed to sit at room temperature for 10 minutes. The plate was incubated overnight at 37° C.

B. Phage Elution

100 μL of phage elution buffer (10 mM Tris-Cl, pH 7.5, 10 mM EDTA, 100 mM NaCl) was added to each well of a sterile U-bottom 96 well plate. A single phage plaque from the overnight library plate was transferred with a filtered pipette tip to a well. The phage elution plate was incubated at 37° C. for 1 hour. The plate may be stored at 4° C. following incubation.

C. Culture for Deep Well Plates

XL1B cells from 50 mL culture were added to 2xYT media at a 1:100 dilution. The cells were grown at 37° C. in a shaker until the A$_{600}$ was between 0.9 to 1.2.

D. Infection with Phage in Deep Well Plates

When the cells reached the appropriate OD, 1M IPTG (1:2000) was added to the XL1B culture. The final concentration of IPTG was 0.5 mM. 750 μL of cell culture was transferred to each well of a 96 well—deep well plate (Fisher Scientific). Each well was inoculated with 25 μL of eluted phage. The deep well plate was placed in the shaker (250 rpm) and incubated overnight at 37° C.

E. Preparing Supernatant for ELISA Screening

Following incubation, the deep well plates were centrifuged at 3,250 rpm for 20 minutes using the Beckman JA-5.3 plate rotor. 50 μL of supernatant was withdrawn from each well for ELISA.

F. Innoculation of 15 mL Liquid Cultures of XL-1 cells

XL-1s were grown at 37° C. in the shaker (250 rpm) in 2xYT containing 10 μg/mL of tetracycline until A$_{600}$=0.9 to 1.2. IPTG was added at a final concentration of 0.5 mM and 15 mL of the culture was tranferred to a 50 mL conical tube for each clone to be characterized. The cells were inoculated with 10 μL of phage from the high titer stock (titer=~10" pfu/mL) and incubated for 1 hour at 37° C. The cells were grown overnight at room temperature with shaking.

G. Isolation of Soluble Fab from Periplasm

The cells were pelleted in an IEC centrifuge at 4,500 rpm for 20 minutes.

Culture medium was removed the pellet was resuspend in 650 μL of resuspension buffer (50 mM Tris, pH 8.0 containing 1 mM EDTA and 500 mM sucrose), vortexed, and placed on ice for 1 hour with gentle shaking. Cellular debris was removed by centrifugation at 9,000 rpm for 10 minutes at 4° C. The supernatent containing the soluble Fabs was collected and stored at 4° C.

Example 4

Framework Modification

There were twelve murine/human wobble residues within the framework at the potential key positions described above. Position 73 in V$_H$ was kept as the murine residue threonine in the humanization library because this position was determined to affect binding. It was noted, however, that threonine at VH 73 is a common human residue in the human germline V$_H$ subgroup 1 and 2.

The framework residues that differed between the TES-C21 sequence and the human template were randomly substituted as described above and then assessed for their potential affect on target binding, and antibody folding. Potential framework residues that may have affected the binding were identified. In this case, they were residues 12, 27, 43, 48, 67, 69 in V$_H$, and 1, 3, 4, 49, 60, 85 in V$_L$ (Kabat number system). (See FIG. 4) It was later demonstrated that only positions 27 and 69 significantly affected binding in the V$_H$ region (clone number 1136-2C).

The primary screen used was a single point ELISA (SPE) using culture media (See description below). The primary screen selected clones that that bind to the antibody's target molecule. Clones that gave equal or better signal than the parent molecule were selected for the next round of screening.

In the second round of screening, individual phage were grown in a 15 ml bacterial culture and periplasmic preparations were used for SPE and ELISA titration assays. The clones that retained higher binding in this assay were further characterized. Once all the selected primary clones were processed, the top 10-15% clones were sequenced and the clones arranged according to sequence. Representatives from each sequence group were compared against each other and the best clones selected. Sequences from these chosen clones were combined and the effects of various combinations were evaluated.

The constructed library was subjected to an ELISA screen for improved binding to the recombinant human IgE, SE44. Clones with binding affinity greater than murine TES-C21 Fab were isolated and sequenced. Clone ID #4, 49, 72, 76, and 136 were further characterized. ELISA titration curves for clone 4, 49, 72, 78, and 136 are shown in FIGS. 5A and 5B indicating that their affinity is similar to the parent, TES-C21. These clones compete with murine TES-C21 for binding to human IgE indicating that the binding epitope was not changed during the humanization process. The humanized Fabs did not bind to FcER1-bound IgE suggesting that it is less likely that the humanized antibodies will crosslink the receptor to cause histamine release when they were constructed into divalent IgG.

Humanized clone 136 retained 5 murine heavy chain framework residues (=94.3% human V$_H$ framework homology), with a 100% human light chain framework selected for by affinity maturation. The inhibition of IgE binding to FcεRI by the humanized Fab was demonstrated (FIG. 6).

Example 5

Single Point ELISA Protocol for Screening anti IgE

Plates were coated with 2 ug/mL sheep anti-human Fd in carbonate coating buffer overnight at 4° C. The coating solution was removedand the plates were blocked with 200 uL/well 3% BSA/PBS for 1 hour at 37° C. After washing the plates 4× with PBS/0.1% TWEEN® (PBST), 50 uL/well Fab sample (i.e., supernatant containing high titer phage and secreted Fab or periplasmic prep from DMB block, or 15 mL prep) was added. Plates were incubated for 1 hour at room temperature followed by washing 4× with PBST. 50 uL/well of biotinylated SE44 at 0.015 ug/mL diluted in 0.5% BSA/PBS and 0.05% TWEEN® was then added. Plates were then incubated for 2 hours at room temperature and washed 4×PBST. 50 uL/well StreptAvidin HRP 1:2000 dilution in 0.5% BSA/PBS and 0.05% TWEEN® was added and the plates incubated 1 hour at room temperature. Plates were washed 6× with PBST. 50 uL/well TMB substrate (sigma) was added to develop and then stopped by adding 50 uL/well 0.2M $H_2SO_4$.

Example 6

ELISA Titration: Anti IgE

Plates were coated with 0.25 ug/mL (for purified Fab 0.1 ug/ml) SE44 in carbonate coating buffer overnight at 4° C. Coating solution was removed and the plates were blocked with 200 uL/well 3% BSA/PBS for 1 hour at 37° C.

The plates were washed 4× with PBS/0.1% TWEEN® (PBST). 50 uL/well Fab (from 15 mL periplasmic prep) was added starting with a dilution of 1:2 and diluting 3 fold serially in 0.5% BSA/PBS and 0.05% TWEEN®20. Plates were incubated for 2 hours at room temperature.

The plates were washed 4× with PBST and 50 uL/well 1:1000 (0.8 ug/ml) dilution of biotin-sheep anti human Fd in 0.5% BSA/PBS and 0.05% TWEEN® 20 was added. The plates were incubated again for 2 hours at room temperature.

Following a wash 4× with PBST, 50 uL/well Neutra-avidin-AP 1:2000 (0.9 ug/ml) in 0.5% BSA/PBS and 0.05% TWEEN® 20 was added and the plates were incubated 1 hour at room temperature.

The plates were washed 4× with PBST. And developed by adding 50 uL/well pNPP substrate. Development was stopped by adding 50 uL/well 3M NaOH. The absorbance of each well was read at 405 nm or 410 nm.

Example 7

Protocol for Affinity Purification of M13 Phage Expressed Soluble Fab

Day 1
Two 500 mL cultures (2xYT) containing 10 mg/mL tetracycline were innoculated with 5 mL overnight stock XL1B and grown at 37° C. to A600=0.9 to 1.2. IPTG was added to a concentration of 0.5 mM. The cell culture was then infected with 200 µL phage per culture and incubated for 1 hour at 37° C. with shaking. Following infection, the cells were grown at 25° C. overnight with shaking.

Day 2
Cells were pelleted at 3500×g for 30 minutes at 4° C. in 250 mL centrifuge tubes. Culture medium was aspirated and the pellets were resuspended in a total of 12-15 mL lysis buffer (Buffer A+protease inhibitor cocktail).
Buffer A: (1 liter)

| 50 mM $NaH_2PO_4$ | 6.9 g $NaH_2PO_4H_2O$ (or 6 g $NaH_2PO_4$) |
|---|---|
| 300 mM NaCl | 17.54 g NaCl |
| 10 mM imidazole | 0.68 g imidazole (MW 68.08) | adjust pH to 8.0 using NaOH

Lysis buffer:
Mix 25 mL of Buffer A with one tablet of Complete Protease Inhibitor Cocktail (Roche, Basel, Switzerland).
Resuspended cells were transferred into a 50 mL conical tube and lysed with 100 µL 100 mg/mL lysozyme by inverting the tube several times until the mixture moves together as a blob (due to the lysis). Cells were sonicated on ice followed by the addition of 10 µL DNase I (about 1000 units) and gently rocked at 4° C. for 30 minutes. Debri was pelleted by centrifugation at 12000×g for 30 minutes at 4° C., using 50 mL centrifuge tubes. Supernatants were transferred to a new conical tube and stored at 4° C.

Ni-NT agarose (Qiagen, Valencis, Calif.) was used to purify the soluble Fabs according to the manufacturer's protocol. The lysate was mixed with Ni-NTA and loaded into a column. The flow through was collected for SDS-PAGE analysis. The column was washed with 20 mL buffer (50 mM $NaH_2PO_4$, 300 mM NaCl, 15 mM imidazole, adjust pH to 8.0 with NaOH) followed by a 20 mL wash with 50 mM $NaH_2PO_4$, 300 mM NaCl, 20 mM imidazole. Fabs were eluted with 6×500 µL elution buffer (50 mM $NaH_2PO_4$, 300 mM NaCl, 450 mM imidazole, adjust pH to 8.0 with NaOH) and analyzed by SDS PAGE. Column fractions were stored at 4° C. Column fractions were analyzed by SDS-PAGE and the fraction with the greatest amount of Fab was selected and dialyzed in PBS at 4° C.

Example 8

Soluble Receptor Assay

A 96 well assay plate suitable for ELISA was coated with 0.05 mL 0.5 µg/mL FcεRI alpha-chain receptor coating buffer (50 mM carbonate/bicarbonate, pH 9.6) for 12 hours at 4-8° C. The wells were aspirated and 250 µL blocking buffer (PBS, 1% BSA, pH 7.2) was added and incubated for 1 hour at 37° C. In a separate assay plate the samples and reference TES-C21 MAbs were titered from 200 to 0.001 µg/mL by 1:4 dilutions with assay buffer (0.5% BSA and 0.05% Tween 20, PBS, pH 7.2) and an equal volume of 100 ng/mL biotinylated IgE was added and the plate incubated for 2-3 hours at 25° C. The FcεRI-coated wells were washed three times with PBS and 0.05% TWEEN 20 and 50 µL from the sample wells were transferred and incubated with agitation for 30 minutes at 25° C. Fifty µL/well of 1 mg/mL Streptavidin-HRP, diluted 1:2000 in assay buffer, was incubated for 30 minutes with agitation and then the plate was washed as before. Fifty µL/well of TMB substrate was added and color was developed. The reaction was stopped by adding an equal volume of 0.2 M $H_2SO_4$ and the absorbance measured at 450 nm.

Example 9

Binding of Antibodies to IgE-Loaded FcER1

Antibody binding to human IgE associated with the alpha-subunit of FcεRI was determined by preincubating with 10

µg/mL human IgE for 30 min at 4° C. Plates were washed three times followed by a one hour incubation with varying concentrations of either murine anti-human IgE mAbs E-10-10 or the humanized Fab variant. Binding of Fabs was detected with a biotin labeled anti human Fd antibody followed by SA-HRP. Murine ab E10-10 was detected by Goat anti murine 1 g Fc HRP-conjugated Ab.

Example 10

Clone Characterization

Each candidate was assayed for binding affinity and positive clones were sequenced. Antibody variants having beneficial mutations in CDR regions that increase binding affinity were further characterized. Assays included Biacore analysis; inhibition of IgE binding to its receptor; and cross linking of receptor bound IgE.

A library of variants was created. The amino acid sequences for the various CDRs which demonstrated improved affinity are depicted in Table 1. FIG. 7 presents high affinity candidates having combinantions of substitutions.

TABLE 1

| CDRL1: | | CDRH1: | |
|---|---|---|---|
| P RASQSIGTNIH | SEQ ID NO 5 | P MYWLE | SEQ ID NO 15 |
| #1 RASRSIGTNIH | SEQ ID NO 6 | #1 WYWLE | SEQ ID NO 16 |
| #2 RASQRIGTNIH | SEQ ID NO 7 | #2 YYWLE | SEQ ID NO 17 |

| CDRL2: | | CDRH2: | |
|---|---|---|---|
| P YASESIS | SEQ ID NO 8 | P EISPGTFTTNYNEKFKA | SEQ ID NO 18 |
| #1 YAYESIS | SEQ ID NO 9 | #1 EIEPGTFTTNYNEKFKA | SEQ ID NO 19 |
| #2 YASESIY | SEQ ID NO 10 | #2 EIDPGTFTTNYNEKFKA | SEQ ID NO 20 |
| #3 YASESDS | SEQ ID NO 11 | #3 EISPDTFTTNYNEKFKA | SEQ ID NO 21 |
| #4 YASESES | SEQ ID NO 12 | #4 EISPETFTTNYNEKFKA | SEQ ID NO 22 |
| | | #5 EISPGTFETNYNEKFKA | SEQ ID NO 23 |
| | | #6 EIEPGTFETNYNEKFKA | SEQ ID NO 24 |
| | | #7 EIDPGTFETNYNEKFKA | SEQ ID NO 25 |

| CDRL3: | | CDRH3: | |
|---|---|---|---|
| P QQSDSWPTT | SEQ ID NO 13 | P FSHFSGSNYDYFDY | SEQ ID NO 26 |
| #1 AASWSWPTT | SEQ ID NO 14 | #1 FSHFSGMNYDYFDY | SEQ ID NO 27 |
| #2 QQSWSWPTT | SEQ ID NO 71 | #2 FSHFSGQNYDYFDY | SEQ ID NO 28 |
| | | #3 FSHFTGSNYDYFDY | SEQ ID NO 29 |

P = Parent

Figure 8B:
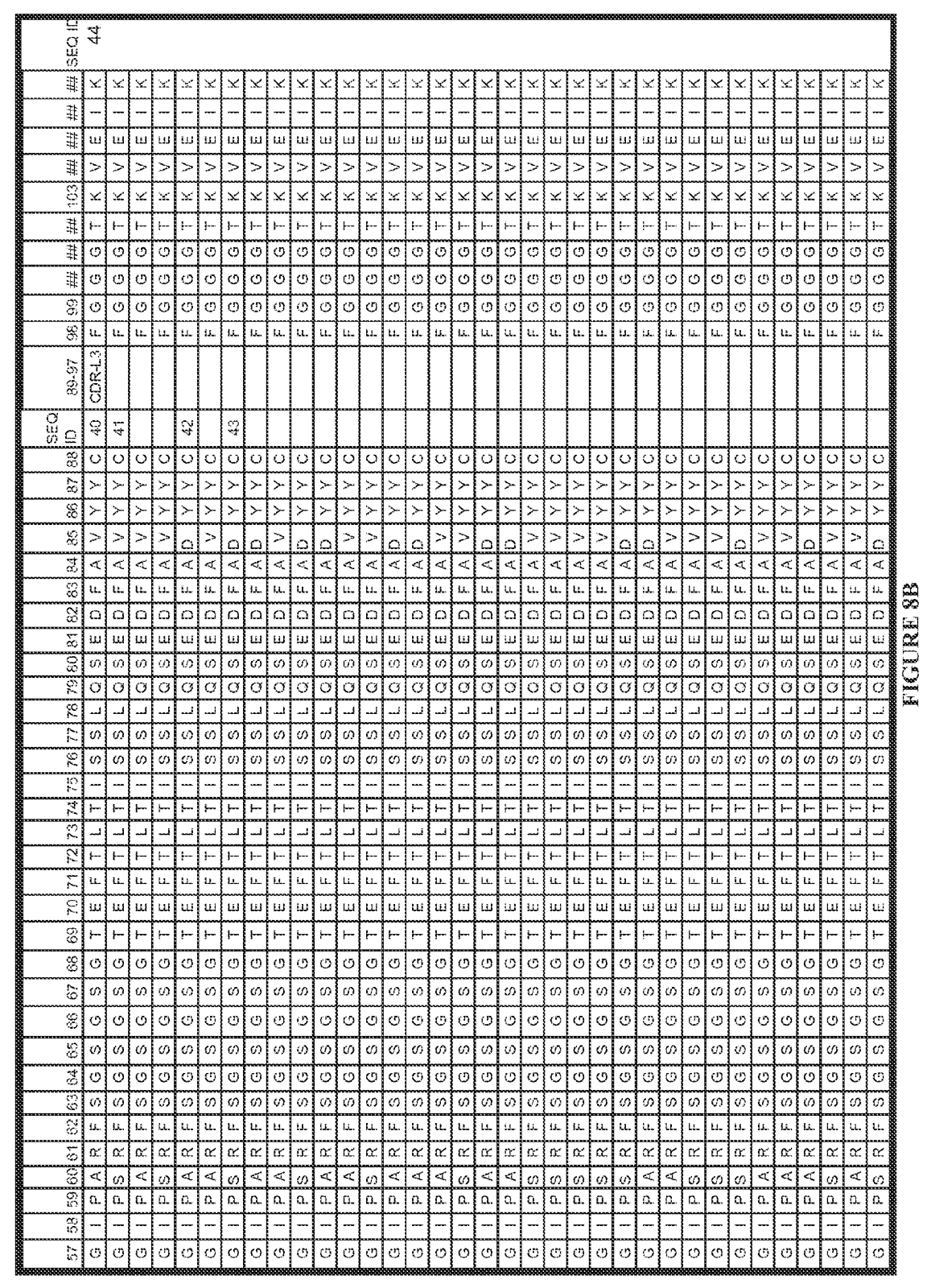

Nineteen heavy chain variants are presented in FIGS. 9 and 35 light chain variants are presented in FIG. 8. Three candidates were further characterized for binding affinity and these are presented in Table 2.

TABLE 2

| | Binding Affinity | |
|---|---|---|
| MAb | Kd | Fold Increase in Binding Affinity |
| TES-C21 | 614 ± 200 pM | |
| MAb 1 (CL-5A) | 0.158 pM | 3886 |
| MAb 2 (CL-2C) | 1.47 ± 0.5 pM | 417 |
| MAb 3 (CL-5I) | 3.2 ± 2.2 pM | 191 |

Example 11

Expression and Purification of Anti-IgE Antibodies and HRP-Conjugation

High affinity MAbs candidates were generated. For the generation of intact anti-IgE MAbs, the heavy and light chains variable regions were PCR amplified from phage vectors templates and subcloned separately into H- and L-chain expression vectors under the expression of a CMV promoter. Six full antibody clones were constructed and are represented in FIG. 10 A-F. Appropriate heavy and light chain plasmids were co-transfected into the mouse myeloma cell line NS0 using electroporation by techniques well known in the art. See, e.g., Liou et al. J. Immunol. 143(12):3967-75 (1989). Antibodies were purified from the single stable cell line supernatants using protein A-sepharose (Pharmacia). The concentration of the antibody was determined using spectrophotometer at 280 nm and FCA assay (IDEXX).

Purified antibodies were conjugated by horseradish peroxidase (HRP) using peroxidase conjugation kit (Zymed Labs, San Francisco, Calif.) according to the manufacturer's protocol. The titer of each conjugated anti-IgE MAb was determined using ELISA with plates coated with a monoclonal human IgE (SE44).

The following cultures have been deposited with the American Type Culture Collection, 10801 University Boulevard, Manassas Va. 20110-2209 USA (ATCC):

| Hybridoma | ATCC NO. | Deposit Date |
|---|---|---|
| Anti-IgE CL-2C | PTA-5678 | Dec. 3, 2003 |
| Anti-IgE CL-5A | PTA-5679 | Dec. 3, 2003 |
| Anti-IgE CL-5I | PTA-5680 | Dec. 3, 2003 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, which assures permanent and unrestricted availability of the progeny of the culture to the public upon issuance of the pertinent U.S. patent.

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as illustration of one aspect of the invention and any culture that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid encoding a variable light chain region of an antibody that specifically binds IgE, said variable light chain region comprising a CDRL1, CDRL2, and CDRL3, wherein the amino acid sequence of CDRL1 consists of SEQ ID NO:5, the amino acid sequence of CDRL2 consists of SEQ ID NO:8, and the amino acid sequence of CDRL3 consists of SEQ ID NO:71.

2. An isolated nucleic acid encoding a variable heavy chain region of an antibody that specifically binds IgE, said variable heavy chain region comprising a CDRH1, CDRH2, and CDRH3, wherein the amino acid sequence of CDRH1 consists of SEQ ID NO:16, the amino acid sequence of CDRH2 consists of SEQ ID NO:25, and the amino acid sequence of CDRH3 consists of SEQ ID NO:26.

3. An isolated nucleic acid encoding a variable light chain region and a variable heavy chain region of an antibody that specifically binds IgE, wherein said variable light chain region comprises a CDRL1, CDRL2, and CDRL3, wherein the amino acid sequence of CDRL1 consists of SEQ ID NO:5, the amino acid sequence of CDRL2 consists of SEQ ID NO:8, and the amino acid sequence of CDRL3 consists of SEQ ID NO:71; and wherein said variable heavy chain region comprises a CDRH1, CDRH2, and CDRH3, wherein the amino acid sequence of CDRH1 consists of SEQ ID NO:16, the amino acid sequence of CDRH2 consists of SEQ ID NO:25, and the amino acid sequence of CDRH3 consists of SEQ ID NO:26.

4. The isolated nucleic acid of claim 1, wherein said nucleic acid encodes a variable light chain region comprising the amino acid sequence set forth in SEQ ID NO:63.

5. The isolated nucleic acid of claim 2, wherein said nucleic acid encodes a variable heavy chain region comprises the amino acid sequence set forth in SEQ ID NO:64.

6. The isolated nucleic acid of claim 3, wherein said nucleic acid encodes a variable light chain region comprising the amino acid sequence set forth in SEQ ID NO:63 and a variable heavy chain region comprising the amino acid sequence set forth in SEQ ID NO:64.

7. A vector comprising the isolated nucleic acid of claim 1.

8. A vector comprising the isolated nucleic acid of claim 2.

9. A vector comprising the isolated nucleic acid of claim 3.

10. An isolated host cell comprising the vector of claim 7.

11. An isolated host cell comprising the vector of claim 8.

12. An isolated host cell comprising the vector of claim 9.

13. An isolated host cell comprising the nucleic acid of claim 7.

14. An isolated host cell comprising the nucleic acid of claim 8.

15. An isolated host cell comprising the nucleic acid of claim 9.

16. A method for producing an antibody comprising culturing the cell of claim 10 under conditions appropriate for the production of said antibody, and isolating the antibody produced.

17. A method for producing an antibody comprising culturing the cell of claim 11 under conditions appropriate for the production of said antibody, and isolating the antibody produced.

18. A method for producing an antibody comprising culturing the cell of claim 12 under conditions appropriate for the production of said antibody, and isolating the antibody produced.

19. A method for producing an antibody comprising culturing the cell of claim 13 under conditions appropriate for the production of said antibody, and isolating the antibody produced.

20. A method for producing an antibody comprising culturing the cell of claim 14 under conditions appropriate for the production of said antibody, and isolating the antibody produced.

21. A method for producing an antibody comprising culturing the cell of claim 15 under conditions appropriate for the production of said antibody, and isolating the antibody produced.

* * * * *

SEQUENCE LISTING

```
<160> NUMBER OF SEQ ID NOS: 71

<210> SEQ ID NO 1
<211> LENGTH: 107
<212> TYPE: PRT
<213> ORGANISM: Mus musculus
<220> FEATURE:
<221> NAME/KEY: misc_feature
<223> OTHER INFORMATION: TES-C21 LIGHT CHAIN

<400> SEQUENCE: 1

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asp Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Glu Phe Thr Leu Asn Ile Asn Ser Val Glu Ser
65                  70                  75                  80

Glu Asp Ile Ala Asp Tyr Tyr Cys Gln Gln Ser Asp Ser Trp Pro Thr
                85                  90                  95

Thr Phe Gly Gly Gly Thr Lys Leu Glu Ile Lys
            100                 105

<210> SEQ ID NO 2
<211> LENGTH: 107
<212> TYPE: PRT
<213> ORGANISM: Homo sapiens
<220> FEATURE:
<221> NAME/KEY: misc_feature
<223> OTHER INFORMATION: L16/-JK4 human light chain consensus sequence
      template

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60
```

```
Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105

<210> SEQ ID NO 3
<211> LENGTH: 123
<212> TYPE: PRT
<213> ORGANISM: Mus musculus
<220> FEATURE:
<221> NAME/KEY: misc_feature
<223> OTHER INFORMATION: TES-C21 Heavy Chain

<400> SEQUENCE: 3

Gln Val Gln Leu Gln Gln Ser Gly Ala Glu Leu Met Lys Pro Gly Ala
 1               5                  10                  15

Ser Val Lys Ile Ser Cys Lys Thr Thr Gly Tyr Thr Phe Ser Met Tyr
                 20                  25                  30

Trp Leu Glu Trp Val Lys Gln Arg Pro Gly His Gly Leu Glu Trp Val
             35                  40                  45

Gly Glu Ile Ser Pro Gly Thr Phe Thr Thr Asn Tyr Asn Glu Lys Phe
 50                  55                  60

Lys Ala Lys Ala Thr Phe Thr Ala Asp Thr Ser Ser Asn Thr Ala Tyr
 65                  70                  75                  80

Leu Gln Leu Ser Gly Leu Thr Ser Glu Asp Ser Ala Val Tyr Phe Cys
                 85                  90                  95

Ala Arg Phe Ser His Phe Ser Gly Ser Asn Tyr Asp Tyr Phe Asp Tyr
                100                 105                 110

Trp Gly Gln Gly Thr Ser Leu Thr Val Ser Ser
            115                 120

<210> SEQ ID NO 4
<211> LENGTH: 113
<212> TYPE: PRT
<213> ORGANISM: Homo sapiens
<220> FEATURE:
<221> NAME/KEY: misc_feature
<223> OTHER INFORMATION: DP88/JH4b human heavy chain consensus sequence
      template

<400> SEQUENCE: 4

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Asp Tyr Leu Val Gln Gly Thr Ser Leu Thr Val Ser
                100                 105                 110

Ser
```

```
<210> SEQ ID NO 5
<211> LENGTH: 11
<212> TYPE: PRT
<213> ORGANISM: ARTIFICIAL
<220> FEATURE:
<223> OTHER INFORMATION: TES-C21 CDRL1 SEQUENCE (TABLE 1)

<400> SEQUENCE: 5

Arg Ala Ser Gln Ser Ile Gly Thr Asn Ile His
1               5                   10

<210> SEQ ID NO 6
<211> LENGTH: 11
<212> TYPE: PRT
<213> ORGANISM: ARTIFICIAL
<220> FEATURE:
<223> OTHER INFORMATION: CDRL1 VARIANT SEQUENCE #1 (TABLE 1)

<400> SEQUENCE: 6

Arg Ala Ser Arg Ser Ile Gly Thr Asn Ile His
1               5                   10

<210> SEQ ID NO 7
<211> LENGTH: 11
<212> TYPE: PRT
<213> ORGANISM: ARTIFICIAL
<220> FEATURE:
<223> OTHER INFORMATION: CDRL1 VARIANT SEQUENCE #2 (TABLE 1)

<400> SEQUENCE: 7

Arg Ala Ser Gln Arg Ile Gly Thr Asn Ile His
1               5                   10

<210> SEQ ID NO 8
<211> LENGTH: 7
<212> TYPE: PRT
<213> ORGANISM: ARTIFICIAL
<220> FEATURE:
<223> OTHER INFORMATION: TES-C21 CDRL2 SEQUENCE (TABLE 1)

<400> SEQUENCE: 8

Tyr Ala Ser Glu Ser Ile Ser
1               5

<210> SEQ ID NO 9
<211> LENGTH: 7
<212> TYPE: PRT
<213> ORGANISM: ARTIFICIAL
<220> FEATURE:
<223> OTHER INFORMATION: CDRL2 VARIANT SEQUENCE #1 (TABLE 1)

<400> SEQUENCE: 9

Tyr Ala Tyr Glu Ser Ile Ser
1               5

<210> SEQ ID NO 10
<211> LENGTH: 7
<212> TYPE: PRT
<213> ORGANISM: ARTIFICIAL
<220> FEATURE:
<223> OTHER INFORMATION: CDRL2 VARIANT SEQUENCE #2 (TABLE 1)

<400> SEQUENCE: 10

Tyr Ala Ser Glu Ser Ile Tyr
1               5
```

```
<210> SEQ ID NO 11
<211> LENGTH: 7
<212> TYPE: PRT
<213> ORGANISM: ARTIFICIAL
<220> FEATURE:
<223> OTHER INFORMATION: CDRL2 VARIANT SEQUENCE #3 (TABLE 1)

<400> SEQUENCE: 11

Tyr Ala Ser Glu Ser Asp Ser
1               5

<210> SEQ ID NO 12
<211> LENGTH: 7
<212> TYPE: PRT
<213> ORGANISM: ARTIFICIAL
<220> FEATURE:
<223> OTHER INFORMATION: CDRL2 VARIANT SEQUENCE #4 (TABLE 1)

<400> SEQUENCE: 12

Tyr Ala Ser Glu Ser Glu Ser
1               5

<210> SEQ ID NO 13
<211> LENGTH: 9
<212> TYPE: PRT
<213> ORGANISM: ARTIFICIAL
<220> FEATURE:
<223> OTHER INFORMATION: TES-C21 CDRL3 (TABLE 1)

<400> SEQUENCE: 13

Gln Gln Ser Asp Ser Trp Pro Thr Thr
1               5

<210> SEQ ID NO 14
<211> LENGTH: 9
<212> TYPE: PRT
<213> ORGANISM: ARTIFICIAL
<220> FEATURE:
<223> OTHER INFORMATION: CDRL3 VARIANT SEQUENCE #1 (TABLE 1)

<400> SEQUENCE: 14

Ala Ala Ser Trp Ser Trp Pro Thr Thr
1               5

<210> SEQ ID NO 15
<211> LENGTH: 5
<212> TYPE: PRT
<213> ORGANISM: ARTIFICIAL
<220> FEATURE:
<223> OTHER INFORMATION: TES-C21 CDRH1

<400> SEQUENCE: 15

Met Tyr Trp Leu Glu
1               5

<210> SEQ ID NO 16
<211> LENGTH: 5
<212> TYPE: PRT
<213> ORGANISM: ARTIFICIAL
<220> FEATURE:
<223> OTHER INFORMATION: CDRH1 VARIANT SEQUENCE #1 (TABLE 1)

<400> SEQUENCE: 16

Trp Tyr Trp Leu Glu
1               5
```

-continued

```
<210> SEQ ID NO 17
<211> LENGTH: 5
<212> TYPE: PRT
<213> ORGANISM: ARTIFICIAL
<220> FEATURE:
<223> OTHER INFORMATION: CDRH1 VARIANT SEQUENCE #2 (TABLE 1)

<400> SEQUENCE: 17

Tyr Tyr Trp Leu Glu
1               5

<210> SEQ ID NO 18
<211> LENGTH: 17
<212> TYPE: PRT
<213> ORGANISM: ARTIFICIAL
<220> FEATURE:
<223> OTHER INFORMATION: TES-C21 CDRH2 (TABLE 1)

<400> SEQUENCE: 18

Glu Ile Ser Pro Gly Thr Phe Thr Thr Asn Tyr Asn Glu Lys Phe Lys
1               5                   10                  15

Ala

<210> SEQ ID NO 19
<211> LENGTH: 17
<212> TYPE: PRT
<213> ORGANISM: ARTIFICIAL
<220> FEATURE:
<223> OTHER INFORMATION: CDRH2 VARIANT SEQUENCE #1 (TABLE 1)

<400> SEQUENCE: 19

Glu Ile Glu Pro Gly Thr Phe Thr Thr Asn Tyr Asn Glu Lys Phe Lys
1               5                   10                  15

Ala

<210> SEQ ID NO 20
<211> LENGTH: 17
<212> TYPE: PRT
<213> ORGANISM: ARTIFICIAL
<220> FEATURE:
<223> OTHER INFORMATION: CDRH2 VARIANT SEQUENCE #2 (TABLE 1)

<400> SEQUENCE: 20

Glu Ile Asp Pro Gly Thr Phe Thr Thr Asn Tyr Asn Glu Lys Phe Lys
1               5                   10                  15

Ala

<210> SEQ ID NO 21
<211> LENGTH: 17
<212> TYPE: PRT
<213> ORGANISM: ARTIFICIAL
<220> FEATURE:
<223> OTHER INFORMATION: CDRH2 VARIANT SEQUENCE #3 (TABLE 1)

<400> SEQUENCE: 21

Glu Ile Ser Pro Asp Thr Phe Thr Thr Asn Tyr Asn Glu Lys Phe Lys
1               5                   10                  15

Ala

<210> SEQ ID NO 22
<211> LENGTH: 17
<212> TYPE: PRT
<213> ORGANISM: ARTIFICIAL
<220> FEATURE:
<223> OTHER INFORMATION: CDRH2 VARIANT SEQUENCE #4 (TABLE 1)
```

```
<400> SEQUENCE: 22

Glu Ile Ser Pro Glu Thr Phe Thr Thr Asn Tyr Asn Glu Lys Phe Lys
1               5                   10                  15

Ala

<210> SEQ ID NO 23
<211> LENGTH: 17
<212> TYPE: PRT
<213> ORGANISM: ARTIFICIAL
<220> FEATURE:
<223> OTHER INFORMATION: CDRH2 VARIANT SEQUENCE #5 (TABLE 1)

<400> SEQUENCE: 23

Glu Ile Ser Pro Gly Thr Phe Glu Thr Asn Tyr Asn Glu Lys Phe Lys
1               5                   10                  15

Ala

<210> SEQ ID NO 24
<211> LENGTH: 17
<212> TYPE: PRT
<213> ORGANISM: ARTIFICIAL
<220> FEATURE:
<223> OTHER INFORMATION: CDRH2 VARIANT SEQUENCE #6 (TABLE 1)

<400> SEQUENCE: 24

Glu Ile Glu Pro Gly Thr Phe Glu Thr Asn Tyr Asn Glu Lys Phe Lys
1               5                   10                  15

Ala

<210> SEQ ID NO 25
<211> LENGTH: 17
<212> TYPE: PRT
<213> ORGANISM: ARTIFICIAL
<220> FEATURE:
<223> OTHER INFORMATION: CDRH2 VARIANT SEQUENCE #7 (TABLE 1)

<400> SEQUENCE: 25

Glu Ile Asp Pro Gly Thr Phe Glu Thr Asn Tyr Asn Glu Lys Phe Lys
1               5                   10                  15

Ala

<210> SEQ ID NO 26
<211> LENGTH: 14
<212> TYPE: PRT
<213> ORGANISM: ARTIFICIAL
<220> FEATURE:
<223> OTHER INFORMATION: TES-C21 CDRH3 (TABLE 1)

<400> SEQUENCE: 26

Phe Ser His Phe Ser Gly Ser Asn Tyr Asp Tyr Phe Asp Tyr
1               5                   10

<210> SEQ ID NO 27
<211> LENGTH: 14
<212> TYPE: PRT
<213> ORGANISM: ARTIFICIAL
<220> FEATURE:
<223> OTHER INFORMATION: CDRH3 VARIANT SEQUENCE #1 (TABLE 1)

<400> SEQUENCE: 27

Phe Ser His Phe Ser Gly Met Asn Tyr Asp Tyr Phe Asp Tyr
1               5                   10
```

```
<210> SEQ ID NO 28
<211> LENGTH: 14
<212> TYPE: PRT
<213> ORGANISM: ARTIFICIAL
<220> FEATURE:
<223> OTHER INFORMATION: CDRH3 VARIANT SEQUENCE #2 (TABLE 1)

<400> SEQUENCE: 28

Phe Ser His Phe Ser Gly Gln Asn Tyr Asp Tyr Phe Asp Tyr
1               5                   10

<210> SEQ ID NO 29
<211> LENGTH: 14
<212> TYPE: PRT
<213> ORGANISM: ARTIFICIAL
<220> FEATURE:
<223> OTHER INFORMATION: CDRH3 VARIANT SEQUENCE #3 (TABLE 1)

<400> SEQUENCE: 29

Phe Ser His Phe Thr Gly Ser Asn Tyr Asp Tyr Phe Asp Tyr
1               5                   10

<210> SEQ ID NO 30
<211> LENGTH: 23
<212> TYPE: PRT
<213> ORGANISM: ARTIFICIAL
<220> FEATURE:
<223> OTHER INFORMATION: FRL1 VARIANT 136 (FIGURE 8)

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 31
<211> LENGTH: 23
<212> TYPE: PRT
<213> ORGANISM: ARTIFICIAL
<220> FEATURE:
<223> OTHER INFORMATION: FRL1 VARIANT 1 (FIGURE 8)

<400> SEQUENCE: 31

Asp Ile Leu Met Thr Gln Ser Pro Ala Thr Leu Ser Val Ser Pro Gly
1               5                   10                  15

Glu Arg Ala Thr Leu Ser Cys
            20

<210> SEQ ID NO 32
<211> LENGTH: 23
<212> TYPE: PRT
<213> ORGANISM: ARTIFICIAL
<220> FEATURE:
<223> OTHER INFORMATION: FRL1 VARIANT 2 (FIGURE 8)

<400> SEQUENCE: 32

Asp Ile Val Leu Thr Gln Ser Pro Ala Thr Leu Ser Val Ser Pro Gly
1               5                   10                  15

Glu Arg Ala Thr Leu Ser Cys
            20

<210> SEQ ID NO 33
<211> LENGTH: 23
<212> TYPE: PRT
<213> ORGANISM: ARTIFICIAL
```

```
<220> FEATURE:
<223> OTHER INFORMATION: FRL1 VARIANT 4 (FIGURE 8)

<400> SEQUENCE: 33

Asp Ile Leu Leu Thr Gln Ser Pro Ala Thr Leu Ser Val Ser Pro Gly
1               5                   10                  15

Glu Arg Ala Thr Leu Ser Cys
            20

<210> SEQ ID NO 34
<211> LENGTH: 23
<212> TYPE: PRT
<213> ORGANISM: ARTIFICIAL
<220> FEATURE:
<223> OTHER INFORMATION: FRL1 VARIANT 13 (FIGURE 8)

<400> SEQUENCE: 34

Glu Ile Val Leu Thr Gln Ser Pro Ala Thr Leu Ser Val Ser Pro Gly
1               5                   10                  15

Glu Arg Ala Thr Leu Ser Cys
            20

<210> SEQ ID NO 35
<211> LENGTH: 23
<212> TYPE: PRT
<213> ORGANISM: ARTIFICIAL
<220> FEATURE:
<223> OTHER INFORMATION: FRL1 VARIANT 18 (FIGURE 8)

<400> SEQUENCE: 35

Glu Ile Leu Leu Thr Gln Ser Pro Ala Thr Leu Ser Val Ser Pro Gly
1               5                   10                  15

Glu Arg Ala Thr Leu Ser Cys
            20

<210> SEQ ID NO 36
<211> LENGTH: 23
<212> TYPE: PRT
<213> ORGANISM: ARTIFICIAL
<220> FEATURE:
<223> OTHER INFORMATION: FRL1 VARIANT 25 (FIGURE 8)

<400> SEQUENCE: 36

Asp Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 37
<211> LENGTH: 23
<212> TYPE: PRT
<213> ORGANISM: ARTIFICIAL
<220> FEATURE:
<223> OTHER INFORMATION: FRL1 VARIANT 27 (FIGURE 8)

<400> SEQUENCE: 37

Glu Ile Leu Met Thr Gln Ser Pro Ala Thr Leu Ser Val Ser Pro Gly
1               5                   10                  15

Glu Arg Ala Thr Leu Ser Cys
            20
```

```
<210> SEQ ID NO 38
<211> LENGTH: 15
<212> TYPE: PRT
<213> ORGANISM: ARTIFICIAL
<220> FEATURE:
<223> OTHER INFORMATION: FRL2 VARIANT 136 (FIGURE 8)

<400> SEQUENCE: 38

Trp Tyr Gln Gln Lys Pro Gly Gln Ala Pro Arg Leu Leu Ile Tyr
1               5                   10                  15

<210> SEQ ID NO 39
<211> LENGTH: 15
<212> TYPE: PRT
<213> ORGANISM: ARTIFICIAL
<220> FEATURE:
<223> OTHER INFORMATION: FRL2 VARIANT 1 (FIGURE 8)

<400> SEQUENCE: 39

Trp Tyr Gln Gln Lys Pro Gly Gln Ala Pro Arg Leu Leu Ile Lys
1               5                   10                  15

<210> SEQ ID NO 40
<211> LENGTH: 32
<212> TYPE: PRT
<213> ORGANISM: ARTIFICIAL
<220> FEATURE:
<223> OTHER INFORMATION: FRL3 VARIANT 136 (FIGURE 8)

<400> SEQUENCE: 40

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30

<210> SEQ ID NO 41
<211> LENGTH: 32
<212> TYPE: PRT
<213> ORGANISM: ARTIFICIAL
<220> FEATURE:
<223> OTHER INFORMATION: FRL3 VARIANT 1 (FIGURE 8)

<400> SEQUENCE: 41

Gly Ile Pro Ser Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30

<210> SEQ ID NO 42
<211> LENGTH: 32
<212> TYPE: PRT
<213> ORGANISM: ARTIFICIAL
<220> FEATURE:
<223> OTHER INFORMATION: FRL3 VARIANT 13 (FIGURE 8)

<400> SEQUENCE: 42

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Asp Tyr Tyr Cys
                20                  25                  30

<210> SEQ ID NO 43
<211> LENGTH: 32
<212> TYPE: PRT
<213> ORGANISM: ARTIFICIAL
```

```
<220> FEATURE:
<223> OTHER INFORMATION: FRL3 VARIANT 18 (FIGURE 8)

<400> SEQUENCE: 43

Gly Ile Pro Ser Arg Phe Ser Gly Ser Gly Ser Gly Thr Glu Phe Thr
1               5                   10                  15

Leu Thr Ile Ser Ser Leu Gln Ser Glu Asp Phe Ala Asp Tyr Tyr Cys
            20                  25                  30

<210> SEQ ID NO 44
<211> LENGTH: 10
<212> TYPE: PRT
<213> ORGANISM: ARTIFICIAL
<220> FEATURE:
<223> OTHER INFORMATION: FRL4 VARIANT (FIGURE 8)

<400> SEQUENCE: 44

Phe Gly Gly Gly Thr Lys Val Glu Ile Lys
1               5                   10

<210> SEQ ID NO 45
<211> LENGTH: 30
<212> TYPE: PRT
<213> ORGANISM: ARTIFICIAL
<220> FEATURE:
<223> OTHER INFORMATION: FRH1 VARIANT 136 (FIGURE 9)

<400> SEQUENCE: 45

Gln Val Gln Leu Val Gln Ser Gly Ala Glu Val Met Lys Pro Gly Ser
1               5                   10                  15

Ser Val Lys Val Ser Cys Lys Ala Ser Gly Tyr Thr Phe Ser
            20                  25                  30

<210> SEQ ID NO 46
<211> LENGTH: 30
<212> TYPE: PRT
<213> ORGANISM: ARTIFICIAL
<220> FEATURE:
<223> OTHER INFORMATION: FRH1 VARIANT 2 (FIGURE 9)

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser
            20                  25                  30

<210> SEQ ID NO 47
<211> LENGTH: 14
<212> TYPE: PRT
<213> ORGANISM: ARTIFICIAL
<220> FEATURE:
<223> OTHER INFORMATION: FRH2 VARIANT 136 (FIGURE 9)

<400> SEQUENCE: 47

Trp Val Arg Gln Ala Pro Gly His Gly Leu Glu Trp Met Gly
1               5                   10

<210> SEQ ID NO 48
<211> LENGTH: 14
<212> TYPE: PRT
<213> ORGANISM: ARTIFICIAL
<220> FEATURE:
<223> OTHER INFORMATION: FRH2 VARIANT 2 (FIGURE 9)
```

```
<400> SEQUENCE: 48

Trp Val Arg Gln Ala Pro Gly Gln Gly Leu Glu Trp Met Gly
1               5                   10

<210> SEQ ID NO 49
<211> LENGTH: 14
<212> TYPE: PRT
<213> ORGANISM: ARTIFICIAL
<220> FEATURE:
<223> OTHER INFORMATION: FRH2 VARIANT 8 (FIGURE 9)

<400> SEQUENCE: 49

Trp Val Arg Gln Ala Pro Gly Gln Gly Leu Glu Trp Val Gly
1               5                   10

<210> SEQ ID NO 50
<211> LENGTH: 14
<212> TYPE: PRT
<213> ORGANISM: ARTIFICIAL
<220> FEATURE:
<223> OTHER INFORMATION: FRH2 VARIANT 21 (FIGURE 9)

<400> SEQUENCE: 50

Trp Val Arg Gln Ala Pro Gly His Gly Leu Glu Trp Val Gly
1               5                   10

<210> SEQ ID NO 51
<211> LENGTH: 32
<212> TYPE: PRT
<213> ORGANISM: ARTIFICIAL
<220> FEATURE:
<223> OTHER INFORMATION: FRH3 VARIANT 136 (FIGURE 9)

<400> SEQUENCE: 51

Arg Val Thr Phe Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 52
<211> LENGTH: 32
<212> TYPE: PRT
<213> ORGANISM: ARTIFICIAL
<220> FEATURE:
<223> OTHER INFORMATION: FRH3 VARIANT 1 (FIGURE 9)

<400> SEQUENCE: 52

Arg Ala Thr Phe Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 53
<211> LENGTH: 32
<212> TYPE: PRT
<213> ORGANISM: ARTIFICIAL
<220> FEATURE:
<223> OTHER INFORMATION: FRH3 VARIANT 43 (FIGURE 9)

<400> SEQUENCE: 53

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

-continued

```
<210> SEQ ID NO 54
<211> LENGTH: 32
<212> TYPE: PRT
<213> ORGANISM: ARTIFICIAL
<220> FEATURE:
<223> OTHER INFORMATION: FRH3 VARIANT 103 (FIGURE 9)

<400> SEQUENCE: 54

Arg Ala Thr Ile Thr Ala Asp Thr Ser Thr Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 55
<211> LENGTH: 11
<212> TYPE: PRT
<213> ORGANISM: ARTIFICIAL
<220> FEATURE:
<223> OTHER INFORMATION: FRH4 VARIANT 136 (FIGURE 9)

<400> SEQUENCE: 55

Trp Gly Gln Gly Thr Leu Val Thr Val Ser Ser
1               5                   10

<210> SEQ ID NO 56
<211> LENGTH: 19
<212> TYPE: PRT
<213> ORGANISM: Bacteriophage M13mp18
<220> FEATURE:
<221> NAME/KEY: misc_feature
<223> OTHER INFORMATION: Gene III signal Sequence

<400> SEQUENCE: 56

Met Glu Trp Ser Gly Val Phe Met Phe Leu Leu Ser Val Thr Ala Gly
1               5                   10                  15

Val His Ser

<210> SEQ ID NO 57
<211> LENGTH: 107
<212> TYPE: PRT
<213> ORGANISM: ARTIFICIAL
<220> FEATURE:
<223> OTHER INFORMATION: LIGHT CHAIN VARIABLE REGION OF CLONE 136

<400> SEQUENCE: 57

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asp Ser Trp Pro Thr
                85                  90                  95

Thr Phe Gly Gly Gly Thr Lys Val Glu Ile Lys
                100                 105
```

<210> SEQ ID NO 58
<211> LENGTH: 106
<212> TYPE: PRT
<213> ORGANISM: ARTIFICIAL
<220> FEATURE:
<223> OTHER INFORMATION: LIGHT CHAIN CONSTANT REGION OF CLONE 136

<400> SEQUENCE: 58

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 59
<211> LENGTH: 123
<212> TYPE: PRT
<213> ORGANISM: ARTIFICIAL
<220> FEATURE:
<223> OTHER INFORMATION: HEAVY CHAIN VARIABLE REGION OF CLONE 136

<400> SEQUENCE: 59

Gln Val Gln Leu Val Gln Ser Gly Ala Glu Val Met Lys Pro Gly Ser
1               5                   10                  15

Ser Val Lys Val Ser Cys Lys Ala Ser Gly Tyr Thr Phe Ser Met Tyr
            20                  25                  30

Trp Leu Glu Trp Val Arg Gln Ala Pro Gly His Gly Leu Glu Trp Met
        35                  40                  45

Gly Glu Ile Ser Pro Gly Thr Phe Thr Thr Asn Tyr Asn Glu Lys Phe
    50                  55                  60

Lys Ala Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser His Phe Ser Gly Ser Asn Tyr Asp Tyr Phe Asp Tyr
            100                 105                 110

Trp Gly Gln Gly Thr Leu Val Thr Val Ser Ser
        115                 120

<210> SEQ ID NO 60
<211> LENGTH: 330
<212> TYPE: PRT
<213> ORGANISM: ARTIFICIAL
<220> FEATURE:
<223> OTHER INFORMATION: CONSTANT REGION OF HUMAN IgG1

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 61
<211> LENGTH: 107
<212> TYPE: PRT
<213> ORGANISM: ARTIFICIAL
<220> FEATURE:
<223> OTHER INFORMATION: LIGHT CHAIN VARIABLE REGION OF CLONE CL-2C

<400> SEQUENCE: 61

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
 50                  55                  60
```

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Trp Ser Trp Pro Thr
                85                  90                  95

Thr Phe Gly Gly Gly Thr Lys Val Glu Ile Lys
            100                 105

<210> SEQ ID NO 62
<211> LENGTH: 123
<212> TYPE: PRT
<213> ORGANISM: ARTIFICIAL
<220> FEATURE:
<223> OTHER INFORMATION: HEAVY CHAIN VARIABLE REGION OF CLONE CL-2C

<400> SEQUENCE: 62

Gln Val Gln Leu Val Gln Ser Gly Ala Glu Val Met Lys Pro Gly Ser
1               5                   10                  15

Ser Val Lys Val Ser Cys Lys Ala Ser Gly Tyr Thr Phe Ser Trp Tyr
                20                  25                  30

Trp Leu Glu Trp Val Arg Gln Ala Pro Gly His Gly Leu Glu Trp Met
            35                  40                  45

Gly Glu Ile Asp Pro Gly Thr Phe Thr Thr Asn Tyr Asn Glu Lys Phe
    50                  55                  60

Lys Ala Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser His Phe Ser Gly Ser Asn Tyr Asp Tyr Phe Asp Tyr
            100                 105                 110

Trp Gly Gln Gly Thr Leu Val Thr Val Ser Ser
        115                 120

<210> SEQ ID NO 63
<211> LENGTH: 107
<212> TYPE: PRT
<213> ORGANISM: ARTIFICIAL
<220> FEATURE:
<223> OTHER INFORMATION: LIGHT CHAIN VARIABLE REGION OF CLONE CL-5I

<400> SEQUENCE: 63

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
                20                  25                  30

Ile His Trp Tyr Gln Gln Lys Pro Gly Gln Ala Pro Arg Leu Leu Ile
            35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Trp Ser Trp Pro Thr
                85                  90                  95

Thr Phe Gly Gly Gly Thr Lys Val Glu Ile Lys
            100                 105

<210> SEQ ID NO 64
<211> LENGTH: 123
<212> TYPE: PRT
<213> ORGANISM: ARTIFICIAL

```
<220> FEATURE:
<223> OTHER INFORMATION: HEAVY CHAIN VARIABLE REGION OF CLONE CL-5I

<400> SEQUENCE: 64

Gln Val Gln Leu Val Gln Ser Gly Ala Glu Val Met Lys Pro Gly Ser
1               5                   10                  15

Ser Val Lys Val Ser Cys Lys Ala Ser Gly Tyr Thr Phe Ser Met Tyr
            20                  25                  30

Trp Leu Glu Trp Val Arg Gln Ala Pro Gly His Gly Leu Glu Trp Met
        35                  40                  45

Gly Glu Ile Asp Pro Gly Thr Phe Glu Thr Asn Tyr Asn Glu Lys Phe
    50                  55                  60

Lys Ala Arg Val Thr Phe Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser His Phe Ser Gly Ser Asn Tyr Asp Tyr Phe Asp Tyr
            100                 105                 110

Trp Gly Gln Gly Thr Leu Val Thr Val Ser Ser
        115                 120

<210> SEQ ID NO 65
<211> LENGTH: 107
<212> TYPE: PRT
<213> ORGANISM: ARTIFICIAL
<220> FEATURE:
<223> OTHER INFORMATION: LIGHT CHAIN VARIABLE REGION OF CLONE CL-5A

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Trp Ser Trp Pro Thr
                85                  90                  95

Thr Phe Gly Gly Gly Thr Lys Val Glu Ile Lys
            100                 105

<210> SEQ ID NO 66
<211> LENGTH: 123
<212> TYPE: PRT
<213> ORGANISM: ARTIFICIAL
<220> FEATURE:
<223> OTHER INFORMATION: HEAVY CHAIN VARIABLE REGION OF CLONE CL-5A

<400> SEQUENCE: 66

Gln Val Gln Leu Val Gln Ser Gly Ala Glu Val Met Lys Pro Gly Ser
1               5                   10                  15

Ser Val Lys Val Ser Cys Lys Ala Ser Gly Tyr Thr Phe Ser Trp Tyr
            20                  25                  30

Trp Leu Glu Trp Val Arg Gln Ala Pro Gly His Gly Leu Glu Trp Met
        35                  40                  45
```

```
Gly Glu Ile Glu Pro Gly Thr Thr Asn Tyr Asn Glu Lys Phe
    50                  55                  60

Lys Ala Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser His Phe Ser Gly Ser Asn Tyr Asp Tyr Phe Asp Tyr
                100                 105                 110

Trp Gly Gln Gly Thr Leu Val Thr Val Ser Ser
            115                 120

<210> SEQ ID NO 67
<211> LENGTH: 107
<212> TYPE: PRT
<213> ORGANISM: ARTIFICIAL
<220> FEATURE:
<223> OTHER INFORMATION: LIGHT CHAIN VARIABLE REGION OF CLONE CL-2B

<400> SEQUENCE: 67

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Trp Ser Trp Pro Thr
                85                  90                  95

Thr Phe Gly Gly Gly Thr Lys Val Glu Ile Lys
            100                 105

<210> SEQ ID NO 68
<211> LENGTH: 123
<212> TYPE: PRT
<213> ORGANISM: ARTIFICIAL
<220> FEATURE:
<223> OTHER INFORMATION: HEAVY CHAIN VARIABLE REGION OF CLONE CL-2B

<400> SEQUENCE: 68

Gln Val Gln Leu Val Gln Ser Gly Ala Glu Val Met Lys Pro Gly Ser
1               5                   10                  15

Ser Val Lys Val Ser Cys Lys Ala Ser Gly Tyr Thr Phe Ser Tyr Tyr
            20                  25                  30

Trp Leu Glu Trp Val Arg Gln Ala Pro Gly His Gly Leu Glu Trp Met
        35                  40                  45

Gly Glu Ile Asp Pro Gly Thr Phe Thr Asn Tyr Asn Glu Lys Phe
    50                  55                  60

Lys Ala Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser His Phe Ser Gly Ser Asn Tyr Asp Tyr Phe Asp Tyr
                100                 105                 110

Trp Gly Gln Gly Thr Leu Val Thr Val Ser Ser
            115                 120
```

```
<210> SEQ ID NO 69
<211> LENGTH: 107
<212> TYPE: PRT
<213> ORGANISM: ARTIFICIAL
<220> FEATURE:
<223> OTHER INFORMATION: LIGHT CHAIN VARIABLE REGION OF CLONE CL-1136-2C

<400> SEQUENCE: 69

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Trp Ser Trp Pro Thr
                85                  90                  95

Thr Phe Gly Gly Gly Thr Lys Val Glu Ile Lys
            100                 105

<210> SEQ ID NO 70
<211> LENGTH: 123
<212> TYPE: PRT
<213> ORGANISM: ARTIFICIAL
<220> FEATURE:
<223> OTHER INFORMATION: HEAVY CHAIN VARIABLE REGION OF CLONE CL-1136-2C

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Met Tyr
            20                  25                  30

Trp Leu Glu Trp Val Arg Gln Ala Pro Gly Gln Gly Leu Glu Trp Met
        35                  40                  45

Gly Glu Ile Ser Pro Gly Thr Phe Thr Thr Asn Tyr Asn Glu Lys Phe
50                  55                  60

Lys Ala Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser His Phe Ser Gly Ser Asn Tyr Asp Tyr Phe Asp Tyr
            100                 105                 110

Trp Gly Gln Gly Thr Leu Val Thr Val Ser Ser
        115                 120

<210> SEQ ID NO 71
<211> LENGTH: 9
<212> TYPE: PRT
<213> ORGANISM: ARTIFICIAL
<220> FEATURE:
<223> OTHER INFORMATION: CDRL3 VARIANT SEQUENCE #2 (TABLE 1)

<400> SEQUENCE: 71

Gln Gln Ser Trp Ser Trp Pro Thr Thr
1               5
```